United States Patent
Tuerk et al.

(10) Patent No.: US 9,426,986 B2
(45) Date of Patent: Aug. 30, 2016

(54) HYPERBRANCHED POLYCARBONATES FOR SOLUBILIZING POORLY SOLUBLE ACTIVE SUBSTANCES

(75) Inventors: Holger Tuerk, Mannheim (DE); Monika Haberecht, Ludwigshafen (DE); Michael Ishaque, Mannheim (DE); Hiroe Yamada, Yokohama (JP); Daniel Schoenfelder, Brussels (BE); Bernd Bruchmann, Freinsheim (DE)

(73) Assignee: BASF SE, Ludwigshafen (DE)

( * ) Notice: Subject to any disclaimer, the term of this patent is extended or adjusted under 35 U.S.C. 154(b) by 532 days.

(21) Appl. No.: 13/319,465

(22) PCT Filed: May 4, 2010

(86) PCT No.: PCT/EP2010/056001
§ 371 (c)(1),
(2), (4) Date: Nov. 8, 2011

(87) PCT Pub. No.: WO2010/130599
PCT Pub. Date: Nov. 18, 2010

(65) Prior Publication Data
US 2012/0054920 A1 Mar. 1, 2012

(30) Foreign Application Priority Data
May 11, 2009 (EP) .................................... 09159881

(51) Int. Cl.
| *A01N 25/30* | (2006.01) |
| *A01N 25/02* | (2006.01) |
| *A61K 9/107* | (2006.01) |
| *A61K 47/34* | (2006.01) |
| *C08G 18/12* | (2006.01) |
| *C08G 18/32* | (2006.01) |
| *C08G 18/44* | (2006.01) |
| *C08G 18/73* | (2006.01) |
| *C08G 18/75* | (2006.01) |
| *C08G 64/02* | (2006.01) |
| *C08G 83/00* | (2006.01) |
| *C08L 101/00* | (2006.01) |

(52) U.S. Cl.
CPC .............. *A01N 25/30* (2013.01); *A01N 25/02* (2013.01); *A61K 9/1075* (2013.01); *A61K 47/34* (2013.01); *C08G 18/12* (2013.01); *C08G 18/3206* (2013.01); *C08G 18/44* (2013.01); *C08G 18/73* (2013.01); *C08G 18/755* (2013.01); *C08G 64/0216* (2013.01); *C08G 83/005* (2013.01); *C08L 101/005* (2013.01)

(58) Field of Classification Search
CPC  C08G 65/2609; C08G 59/24; C09D 163/00; C07D 303/28
USPC ........ 525/403, 462; 528/370, 405, 418, 421; 504/358, 360, 362; 514/772.7; 424/486
See application file for complete search history.

(56) References Cited

U.S. PATENT DOCUMENTS

| 2008/0040786 | A1 | 2/2008 | Chang |
| 2008/0167430 | A1 | 7/2008 | Bruchmann et al. |
| 2009/0030140 | A1 | 1/2009 | Eipper et al. |
| 2009/0099319 | A1 | 4/2009 | Stumbe et al. |
| 2009/0209701 | A1 | 8/2009 | Steinmetz et al. |
| 2010/0028582 | A1 | 2/2010 | Joch et al. |
| 2010/0048655 | A1 | 2/2010 | Koltzenburg et al. |
| 2011/0105333 | A1* | 5/2011 | Israels et al. ................ 504/360 |

FOREIGN PATENT DOCUMENTS

| JP | H 03220233 | 9/1991 |
| JP | 2009235291 | 10/2009 |
| WO | WO2005/075565 | 8/2005 |
| WO | WO 2006/038110 | 4/2006 |
| WO | WO 2006/089940 | 8/2006 |
| WO | WO 2007/125028 | 11/2007 |
| WO | WO 2007/134736 | 11/2007 |
| WO | WO 2008/009516 | 1/2008 |
| WO | WO 2008/040786 | 4/2008 |
| WO | WO 2009/021986 | 2/2009 |

OTHER PUBLICATIONS

Dow, Voranol® Polyether Polyols, 2003, p. 1-3.*
IUPAC Compendium of Chemical Terminology, entry for Amphiphilic, 2014.*
International Search Report in International Application No. PCT/EP2010/056001, filed May 4, 2010.
English language translation of the International Preliminary Report on Patentability from corresponding International Application No. PCT/EP2010/056001, filed May 4, 2010.

* cited by examiner

Primary Examiner — Robert Jones, Jr.
(74) Attorney, Agent, or Firm — Brinks Gilson & Lione

(57) ABSTRACT

The present invention provides a composition comprising an amphiphile and an active ingredient whose solubility in water at 20° C. is not more than 10 g/L. Likewise provided is an amphiphile comprising a hyperbranched polycarbonate which is joined to at least one linear or comb-type polymer, a process for preparing the amphiphile, and the use of the amphiphile in compositions comprising an active ingredient whose solubility in water at 20° C. is not more than 10 g/L.

16 Claims, No Drawings

HYPERBRANCHED POLYCARBONATES FOR SOLUBILIZING POORLY SOLUBLE ACTIVE SUBSTANCES

This application is a National Stage application of International Application No. PCT/EP2010/056001, filed May 4, 2010, the entire contents of which is hereby incorporated herein by reference. This application also claims priority under 35 U.S.C. §119 to European Patent Application No. 09159881.3, filed May 11, 2009, the entire contents of which is hereby incorporated herein by reference.

The present invention provides a composition comprising an amphiphile and an active ingredient whose solubility in water at 20° C. is not more than 10 g/L. Likewise provided is an amphiphile comprising a hyperbranched polycarbonate which is joined to at least one linear or comb-type polymer, a process for preparing the amphiphile, and the use of the amphiphile in compositions comprising an active ingredient whose solubility in water at 20° C. is not more than 10 g/L. Additionally provided is the use of the amphiphile for controlling phytopathogenic fungi and/or unwanted plant growth and/or unwanted insect or mite infestation and/or for regulating the growth of plants, and also plant propagation material comprising the amphiphile. Combinations of preferred features with other preferred features are embraced by the present invention.

Many cases require hydrophobic active ingredients to be solubilized in water without causing any chemical change to the active ingredient in question as such. For this purpose it is possible, for example, to prepare an emulsion, with the active ingredient in question being situated in the oil phase of the emulsion. For many active pharmaceutical ingredients or crop protection agents, however, especially those which are to be transported with a body fluid or in the sap of a plant, a procedure of this kind is not possible. Under the action of high shearing forces, emulsions may break. Moreover, sterilizing while maintaining the emulsion is in many cases not possible.

Compositions comprising an amphiphile and a sparingly soluble active ingredient are common knowledge: WO 2007/125028 discloses a method of solubilizing hydrophobic active ingredients in an aqueous medium using as an auxiliary a hyperbranched polymer obtainable by preparing a hyperbranched polyester on the basis of a dicarboxylic, tricarboxylic or tetracarboxylic acid and a diol or triol and reacting the polyester with a polyalkylene oxide unit. WO 2009/021986 discloses a seed dressing comprising an active ingredient and a hyperbranched polymer, which may be a hyperbranched polycarbonate, for example.

A disadvantage of the known amphiphiles for solubilizing hydrophobic active ingredients in aqueous media is that they are able to solubilize only small amounts of active ingredient. Moreover, the amphiphiles themselves are often not water-soluble or water-dispersible, and so are not suitable for solubilization in aqueous media. Polyester-containing amphiphiles have the disadvantage, moreover, that they are themselves in some cases sensitive to hydrolysis, particularly as a result of the terminal acid groups present.

Polycarbonates are typically obtained from the reaction of alcohols or phenols with phosgene or from the reaction of alcohols or phenols with dialkyl or diaryl carbonates. Important industrially are aromatic polycarbonates which are prepared, for example, from bisphenols; in terms of market volume, aliphatic polycarbonates have to date played a minor part. The aromatic or aliphatic polycarbonates described in the literature are generally of linear construction or constructed with only a low degree of branching. Hyperbranched polycarbonates as well, however, are common knowledge: WO 2006/089940 discloses water-emulsifiable hyperbranched polycarbonates which at least in part are reacted directly with a monofunctional polyalkylene oxide polyether alcohol. WO 2005/075565 discloses the reaction of a hyperbranched polycarbonate with a functionalizing reagent that is able to react with the OH and/or carbonate groups or carbamoyl groups of the polycarbonate. WO 2007/134736 and WO 2008/009516 disclose the reaction of a hyperbranched polycarbonate with a functionalizing reagent which is able to react with the OH and/or carbonate groups or carbamoyl groups of the polycarbonate. An example given is the reaction with compounds comprising anhydride groups, allowing polycarbonates to be obtained that comprise acid groups.

It was an object of the present invention to find an alternative amphiphile suitable for solubilizing sparingly soluble active ingredients in an aqueous medium. A further object was to find an amphiphile which is able to solubilize very high quantities of active ingredient, especially active agrochemical ingredient. Moreover, the amphiphile ought itself to be water-soluble or water-dispersible. A further object, finally, was to find an amphiphile which is less sensitive to hydrolysis than polyesters.

The object has been achieved by means of a composition comprising an amphiphile and an active ingredient whose solubility in water at 20° C. is not more than 10 g/L, the amphiphile comprising a hyperbranched polycarbonate.

The solubility of the active ingredient in water at 20° C. is not more than 10 g/L, preferably not more than 2 g/l, more preferably not more than 0.5 g/l, and especially not more than 0.1 g/l. The composition may comprise one or more different active ingredients. Examples of active ingredients are active agrochemical ingredients, active cosmetic ingredients, active pharmaceutical ingredients or nutritional supplements (such as vitamins and carotenoids). Preferred active ingredients are active agrochemical ingredients.

Examples of active cosmetic ingredients are cosmetic oils, aromas and flavors, vitamins or UV absorbers. Cosmetic oils include peanut oil, jojoba oil, coconut oil, almond oil, olive oil, palm oil, castor oil, soybean oil or wheatgerm oil, or essential oils such as dwarf pine oil, lavender oil, rosemary oil, spruce needle oil, pine needle oil, eucalyptus oil, peppermint oil, sage oil, bergamot oil, turpentine oil, balm oil, juniper oil, lemon oil, anise oil, cardamom oil, camphor oil, etc., or mixtures thereof. UV absorbers include 2-hydroxy-4-methoxybenzophenone, 2,2',4,4'-tetrahydroxybenzophenone, 2,2'-dihydroxy-4,4'-dimethoxybenzophenone, 2,4-dihydroxybenzophenone, 2'-ethylhexyl 2-cyano-3,3-diphenylacrylate, 2,4,6-trianilino-p-(carbo-2'-ethylhexyl-1'-oxy)-1,3,5-triazine, 3-(4-methoxybenzylidene)camphor, 2-ethylhexyl N,N-dimethyl-4-aminobenzoate, 3,3,5-trimethylcyclohexyl salicylate, 4-isopropyldibenzoylmethane, 2-ethylhexyl p-methoxycinnamate, and 2-isoamyl p-methoxycinnamate, and mixtures thereof.

Examples of aromas and flavors are as described in WO 01/49817 or in "Flavors and Fragrances", Ullmann's Encyclopedia of Industrial Chemistry, Wiley-VCH, 2002, hereby incorporated by reference.

Examples of vitamins are vitamins, provitamins and vitamin precursors form the groups A, C, E, and F, more particularly 3,4-didehydroretinol, beta-carotene (provitamin of vitamin A), ascorbic acid (vitamin C), and the palmitic esters, glucosides or phosphates of ascorbic acid, tocopherols, more particularly alpha-tocopherol and its esters, such as the acetate, nicotinate, phosphate, and succinate, for example; and also vitamin F, which is understood to constitute essential fatty acids, particularly linoleic acid, linolenic acid, and arachidonic acid.

Examples of active pharmaceutical ingredients include the following: benzodiazepines, antihypertensives, vitamins, cytostatics—especially taxol, anesthetics, neuroleptics, antidepressants, antivirals, such as anti-HIV agents, antibiotics, antimycotics, antidementia drugs, fungicides, chemotherapeutic agents, urologicals, platelet aggregation inhibitors, sulfonamides, spasmolytics, hormones, immunoglobulins, sera, thyroid therapeutics, psychoactive drugs, anti-Parkinson agents and other anti-hyperkinetics, ophthalmologicals, neuropathy products, calcium metabolism regulators, muscle relaxants, anesthetics, lipid-lowering agents, hepatotherapeutics, coronary agents, cardiac agents, immunotherapeutics, regulatory peptides and their inhibitors, hypnotics, sedatives, gynaecologicals, gout remedies, fibrinolytics, enzyme products and transport proteins, enzyme inhibitors, emetics, blood flow stimulators, diuretics, diagnostic aids, corticoids, cholinergics, biliary therapeutics, antasthmatics, bronchodilators, beta-receptor blockers, calcium antagonists, ACE inhibitors, arteriosclerosis remedies, antiinflammatories, anticoagulants, antihypotensives, antihypoglycemics, antihypertensives, antifibrinolytics, antiepileptics, antiemetics, antidotes, antidiabetics, anti-arrythmics, antianemics, antiallergics, antelmintics, analgesics, analeptics, aldosterone antagonists, slimming agents.

The term "active agrochemical ingredients" (also called pesticides below) refers to at least one active ingredient selected from the group of fungicides, insecticides, nematicides, herbicides, safeners and/or growth regulators. Preferred pesticides are fungicides, insecticides and herbicides, especially fungicides. Mixtures of pesticides from two or more of the aforementioned classes can also be used. The skilled person is familiar with such pesticides, which can be found in Pesticide Manual, 14th Ed. (2006), The British Crop Protection Council, London, for example. Suitable insecticides are insecticides from the class of the carbamates, organophosphates, organochlorine insecticides, phenylpyrazoles, pyrethroids, neonicotinoids, spinosins, avermectins, milbemycins, juvenile hormone analogues, alkyl halides, organotin compounds, nereistoxin analogues, benzoylureas, diacylhydrazines, METI acaricides, and also insecticides such as chloropicrin, pymetrozine, flonicamid, clofentezine, hexythiazox, etoxazole, diafenthiuron, propargite, tetradifon, chlorfenapyr, DNOC, buprofezine, cyromazine, amitraz, hydramethylnon, acequinocyl, fluacrypyrim, rotenone or derivatives thereof. Suitable fungicides are fungicides from the classes of the dinitroanilines, allylamines, anilinopyrimidines, antibiotics, aromatic hydrocarbons, benzenesulfonamides, benzimidazoles, benzisothiazoles, benzophenones, benzothiadiazoles, benzotriazines, benzylcarbamates, carbamates, carboxamides, carboxylic acid amdides, chloronitriles, cyanoacetamide oximes, cyanoimidazoles, cyclopropanecarboxamides, dicarboximides, dihydrodioxazines, dinitrophenylcrotonates, dithiocarbamates, dithiolanes, ethylphosphonates, ethylaminothiazole carboxamides, guanidines, hydroxyl(2-amino)pyrimidines, hydroxyanilides, imidazoles, imidazolinones, inorganics, isobenzofuranones, methoxyacrylates, methoxycarbamates, morpholines, N-phenylcarbamates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinone hydrazones, pyrroloquinolinones, quinazolinones, quinolines, quinones, sulfamides, sulfamoyltriazoles, thiazolecarboxamides, thiocarbamates, thiocarbamates, thiophanates, thiophenecarboxamides, toluamides, triphenyltin compounds, triazines, triazoles. Suitable herbicides are herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ethers, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolinones, triazolocarboxamides, triazolopyrimidines, triketones, uracils, ureas.

In one embodiment the pesticide comprises an insecticide, and preferably the pesticide is composed of at least one insecticide. Preferred insecticides are fipronil, allethrin, alpha-cypermethrin, beta-cyfluthrin, bifenthrin, bioallethrin, 4-chloro-2-(2-chloro-2-methylpropyl)-5-[(6-iodo-3-pyridinyl)methoxy]-3(2H)-pyridazinone (CAS RN: 120955-77-3), chlorfenapyr, chlorpyrifos, cyfluthrin, cyhalothrin, cypermethrin, deltamethrin, etofenprox, fenoxycarb, flufenoxuron, hydramethylnon, metaflumizone, permethrin, pyriproxifen, silafluofen, tebufenocide, and tralomethrin. Particularly preferred insecticides are fipronil, alpha-cypermethrin, bifenthrin, chlorfenapyr, cyfluthrin, cypermethrin, deltamethrin, etofenprox, hydramethylnon, metaflumizone, permethrin. Especially preferred insecticides are fipronil, alpha-cypermethrin, deltamethrin, chlorfe-napyr, hydramethylnon, and metaflumizone. An especially preferred insecticide is fipronil. In another embodiment the pesticide comprises a fungicide, and preferably the pesticide is composed of at least one fungicide. Preferred fungicides are pyraclostrobin, metconazole, and epoxiconazole. In another embodiment the pesticide comprises a herbicide, and preferably the pesticide is composed of at least one herbicide. In another embodiment the pesticide comprises a growth regulator, and preferably the pesticide is composed of at least one growth regulator.

The composition of the invention comprises typically 0.1% to 70% by weight of active ingredient, preferably 1% to 50% by weight, more particularly 3% to 30% by weight, based on the composition.

Amphiphiles typically comprise at least one polar (hydrophilic) moiety and at least one apolar (hydrophobic) moiety. Typical amphiphiles are fatty acids, surfactants, and phospholipids. The composition may comprise one or more different amphiphiles.

By hyperbranched polycarbonates for the purposes of this invention are meant noncrosslinked macromolecules having hydroxyl and carbonate or carbamoyl chloride groups, which may be both structurally and molecularly nonuniform. On the one hand they may be synthesized starting from a central molecule in the same way as for dendrimers but, in contrast to the latter, with a nonuniform chain length of the branches. Hyperbranched polymers are therefore to be differentiated from dendrimers (U.S. Pat. No. 6,399,048).

For the purposes of the present invention, hyperbranched polymers do not comprise dendrimers. On the other hand, the hyperbranched polymers may also be of linear construction, with functional, branched side groups, or else, as a combination of the two extremes, may include linear and branched molecule moieties. For the definition of dendrimers and hyperbranched polymers see also P. J. Flory, J. Am. Chem. Soc. 1952, 74, 2718 and H. Frey et al., Chem. Eur. J. 2000, 6, 2499.

By "hyperbranched" in the context of the present invention is meant that the degree of branching (DB), in other words the ratio of the sum of the average number of dendritic linkages plus the average number of end groups to the sum of the average number of dendritic and linear linkages plus the average number of end groups, per molecule, multiplied by 100, is 10% to 99.9%, preferably 20% to 99%, more preferably 20% to 95%. By "dendrimeric" in the context of the present invention is meant that the degree of branching is 99.9%-100%. For the definition of the degree of branching see H. Frey et al., Acta Polym. 1997, 48, 30.

It is an advantage of the present invention that the polycarbonates of the invention are noncrosslinked. "Noncrosslinked" for the purposes of this specification means that the degree of crosslinking present is less than 15% by weight, preferably less than 10% by weight, determined via the insoluble fraction of the polymer. The insoluble fraction of the polymer was determined by four-hour extraction with the same solvent as used for the gel permeation chromatography for determining the molecular weight distribution of the polymers, i.e., tetrahydrofuran, dimethylacetamide or hexafluoroisopropanol, according to which solvent has the better solvency for the polymer, in a Soxhlet apparatus and, after drying of the residue to constant weight, by weighing of the residue remaining.

The hyperbranched polycarbonate is typically obtainable by
a) preparing a condensation product (K) by reacting an organic carbonate (A) or a phosgene derivative with an alcohol (B1) which has at least three hydroxyl groups, and
b) intermolecularly converting K to the hyperbranched polycarbonate,
the quantitative ratio of the OH groups to the carbonate or phosgene groups being selected such that K has an average of either i) one carbonate or carbamoyl chloride group and more than one OH group, or ii) one OH group and more than one carbonate or carbamoyl group. The polycarbonate is preferably obtained in this way.

The condensation product (K) can be prepared using an organic carbonate (A) or a phosgene derivative. Examples of suitable phosgene derivatives are phosgene, diphosgene or triphosgene, preferably phosgene. It is preferred to use an organic carbonate.

The radicals R in the organic carbonates (A) of the general formula $RO[(CO)O]_nR$ that are used as starting material are each independently of one another a straight-chain or branched aliphatic, aromatic/aliphatic (araliphatic) or aromatic hydrocarbon radical having 1 to 20 C atoms. The two radicals R may also be joined to one another to form a ring. The two radicals R may be the same or different; they are preferably the same. The radical in question is preferably an aliphatic hydrocarbon radical and more preferably a straight-chain or branched alkyl radical having 1 to 5 C atoms, or a substituted or unsubstituted phenyl radical. R in this case is a straight-chain or branched, preferably straight-chain (cyclo)aliphatic, aromatic/aliphatic or aromatic, preferably (cyclo)aliphatic or aromatic, more preferably aliphatic hydrocarbon radical having 1 to 20 C atoms, preferably 1 to 12, more preferably 1 to 6, and very preferably 1 to 4 carbon atoms. Examples of such radicals are methyl, ethyl, isopropyl, n-propyl, n-butyl, isobutyl, sec-butyl, tert-butyl, n-hexyl, n-heptyl, n-octyl, n-decyl, n-dodecyl, n-tetradecyl, n-hexadecyl, n-octadecyl, n-eicosyl, 2-ethylhexyl, cyclopentyl, cyclohexyl, cyclooctyl, cyclododecyl, phenyl, o- or p-tolyl or naphthyl. Methyl, ethyl, n-butyl, and phenyl are preferred. These radicals R may be the same or different; they are preferably the same. The radicals R may also be joined to one another to form a ring. Examples of divalent radicals R of this kind are 1,2-ethylene, 1,2-propylene, and 1,3-propylene. Generally speaking, n is an integer from 1 to 5, preferably from 1 to 3, more preferably from 1 to 2. The carbonates may preferably be simple carbonates of the general formula RO(CO)OR, i.e. n in this case is 1.

Examples of suitable carbonates comprise aliphatic, aromatic/aliphatic or aromatic carbonates such as ethylene carbonate, 1,2- or 1,3-propylene carbonate, diphenyl carbonate, ditolyl carbonate, dixylyl carbonate, dinaphthyl carbonate, ethyl phenyl carbonate, dibenzyl carbonate, dimethyl carbonate, diethyl carbonate, di-n-propyl carbonate, di-n-butyl carbonate, diisobutyl carbonate, dipentyl carbonate, dihexyl carbonate, dicyclohexyl carbonate, diheptyl carbonate, dioctyl carbonate, didecyl carbonate or didodecyl carbonate. Examples of carbonates in which n is greater than 1 comprise dialkyl dicarbonates, such as di-tert-butyl dicarbonate, or dialkyl tricarbonates such as di-tert-butyl tricarbonate. One preferred aromatic carbonate is diphenyl carbonate. Preference is given to aliphatic carbonates, more particularly those in which the radicals comprise 1 to 5 C atoms, such as dimethyl carbonate, diethyl carbonate, di-n-propyl carbonate, di-n-butyl carbonate or diisobutyl carbonate, for example. Diethyl carbonate is especially preferred.

The alcohol (B1) which has at least three hydroxyl groups is usually an aliphatic or aromatic alcohol, or a mixture or two or more different alcohols of this kind. The alcohol (B1) may be branched or unbranched, substituted or unsubstituted, and have 3 to 26 carbon atoms. It is preferably an aliphatic alcohol. Examples of compounds having at least three OH groups comprise glycerol, trimethylolmethane, trimethylolethane, trimethylolpropane, trimethylolbutane, 1,2,4-butanetriol, 1,2,3-hexanetriol, 1,2,4-hexanetriol, tris(hydroxymethyl)amine, tris(hydroxyethyl)amine, tris(hydroxy-propyl)amine, pentaerythritol, diglycerol, triglycerol, polyglycerols, bis(trimethylolpropane), tris(hydroxymethyl) isocyanurate, tris(hydroxyethyl)isocyanurate, phloroglucinol, trihydroxytoluene, trihydroxydimethylbenzene, phloroglucides, hexahydroxybenzene, 1,3,5-benzenetrimethanol, 1,1,1-tris(4'-hydroxyphenyl)methane, 1,1,1-tris(4'-hydroxyphenyl)ethane, sugars, for example glucose, sugar derivatives, for example sorbitol, mannitol, diglycerol, threitol, erythritol, adonitol (ribitol), arabitol (lyxitol), xylitol, dulcitol (galactitol), maltitol, isomalt, or polyesterol. In addition, B1 may be a trifunctional or higher-functionality polyetherol based on alcohols which have at least three OH groups, and $C_2$-$C_{24}$ alkylene oxide. The polyetherol comprises usually one to 30, preferably one to 20, more preferably one to 10 and most preferably one to eight molecules of ethylene oxide and/or propylene oxide and/or isobutylene oxide per hydroxyl group.

The hyperbranched polycarbonate preferably comprises an alcohol (B1) which is a trifunctional or higher-functionality polyetherol based on alcohols which have at least three OH groups, and $C_3$-$C_{24}$ alkylene oxide. Suitable alcohols which have at least three OH groups are as described above, preferably glycerol, trimethylolethane, trimethylolpropane, 1,2,4-butanetriol, 1,2,3-hexanetriol, 1,2,4-hexanetriol, pentaerythritol, more preferably glycerol or trimethylolpropane. Preferred $C_3$-$C_{24}$ alkylene oxides include propylene oxide, butylene oxide, pentylene oxide and mixtures thereof, more preferably propylene oxide. The trifunctional or higher-functionality polyetherols usually comprise at least one to 30, preferably two to 30, more preferably three to 20 $C_3$-$C_{24}$ alkylene oxide molecules in polymerized form. A particularly preferred alcohol (B1) is a trifunctional polyetherol based on glycerol, trimethylolethane, trimethylolpropane, 1,2,4-butanetriol and/or pentaerythritol, and propylene oxide, where the polyetherol comprises at least three, preferably three to 30, more preferably three to 20, molecules of propylene oxide in polymerized form.

In addition to the alcohol (B1), the polycarbonate may have a difunctional alcohol (B2) as a forming component, with the proviso that the mean OH functionality of all alcohols B used together is greater than 2. The alcohols (B1) and (B2) are referred to here together as (B). Suitable difunctional alcohols B2 include diethylene glycol, triethylene glycol, 1,2- and 1,3-propanediol, dipropylene glycol, tripropylene glycol, neopentyl glycol, 1,2-, 1,3- and 1,4-butanediol, 1,2-, 1,3- and 1,5-pentanediol, 1,6-hexanediol, 1,2- or 1,3-cyclopentanediol, 1,2-, 1,3- or 1,4-cyclohexanediol, 1,1-, 1,2-, 1,3- or 1,4-cyclohexanedimethanol, bis(4-hydroxycyclohexyl)methane, bis(4-hydroxy-cyclohexyl) ethane, 2,2-bis(4-hydroxycyclohexyl)propane, 1,1'-bis(4-hydroxyphenyl)-3,3,5-trimethylcyclohexane, resorcinol, hydroquinone, 4,4'-dihydroxybiphenyl, bis(4-hydroxyphenyl)sulfide, bis(4-hydroxyphenyl)sulfone, bis(hydroxymethyl)benzene, bis(hydroxymethyl)toluene, bis(p-hydroxyphenyl)methane, bis(p-hydroxyphenyl)ethane, 2,2-bis(p-hydroxyphenyl)propane, 1,1-bis(p-hydroxyphenyl)cyclohexane, dihydroxy-benzophenone, difunctional polyetherpolyols based on ethylene oxide, propylene oxide, butylene oxide or mixtures thereof, polytetrahydrofuran having a molar mass of 162 to 2000, polycaprolactone or polyesterols based on diols and dicarboxylic acids. Preferred difunctional alcohols (B2) are difunctional polyetherpolyols based on ethylene oxide, propylene oxide, butylene oxide or mixtures thereof, and polyesterols based on diols and dicarboxylic acids.

The diols serve for fine adjustment of the properties of the polycarbonate. If difunctional alcohols are used, the ratio of difunctional alcohols (B2) to the at least trifunctional alcohols (B1) is fixed by the person skilled in the art according to the desired properties of the polycarbonate. In general, the amount of the alcohol(s) (B2) is 0 to 50 mol % based on the total amount of all alcohols (B1) and (B2) together. The amount is preferably 0 to 35 mol %, more preferably 0 to 25 mol % and most preferably 0 to 10 mol %.

The reaction of phosgene, diphosgene or triphosgene with the alcohol or alcohol mixture is generally effected with elimination of hydrogen chloride; the reaction of the carbonates with the alcohol or alcohol mixture to give the inventive high-functionality highly branched polycarbonate is effected with elimination of the monofunctional alcohol or phenol from the carbonate molecule.

After this reaction, i.e. without any further modification, the hyperbranched polycarbonate has high-functionality termination with hydroxyl groups and with carbonate groups or carbamoyl chloride groups. A high-functionality polycarbonate is understood in the context of this invention to mean a product which, as well as the carbonate groups which form the polymer skeleton, additionally has, in terminal or lateral position, at least three, preferably at least four and more preferably at least six functional groups. The functional groups are carbonate groups or carbamoyl chloride groups and/or OH groups. There is in principle no upper limit in the number of terminal or lateral functional groups, but products with a very high number of functional groups may have undesired properties, for example high viscosity or poor solubility. The high-functionality polycarbonates of the present invention usually have not more than 500 terminal or lateral functional groups, preferably not more than 100 terminal or lateral functional groups.

In the preparation of the high-functionality polycarbonates, it is necessary to adjust the ratio of the compounds comprising OH groups to phosgene or carbonate (A) such that the resulting simplest condensation product (known hereinafter as condensation product (K)) comprises an average of either i) one carbonate or carbamoyl chloride group and more than one OH group or ii) one OH group and more than one carbonate or carbamoyl chloride group, preferably an average of either i) one carbonate or carbamoyl chloride group and at least two OH groups or ii) one OH group and at least two carbonate or carbamoyl chloride groups.

It may additionally be advisable, for fine adjustment of the properties of the polycarbonate, to use at least one difunctional carbonyl-reactive compound (A1). This is understood to mean those compounds which have two carbonate and/or carboxyl groups. Carboxyl groups may be carboxylic acids, carbonyl chlorides, carboxylic anhydrides or carboxylic esters, preferably carboxylic anhydrides or carboxylic esters and more preferably carboxylic esters. If such difunctional compounds (A1) are used, the ratio of (A1) to the carbonates or phosgenes (A) is fixed by the person skilled in the art according to the desired properties of the polycarbonate. In general, the amount of the difunctional compound(s) (A1) is 0 to 40 mol % based on the total amount of all carbonates/phosgenes (A) and compounds (A1) together. Preferably the amount is 0 to 35 mol %, more preferably 0 to 25 mol %, and very preferably 0 to 10 mol %. Examples of compounds (A1) are dicarbonates or dicarbamoyl chlorides of diols, examples of which are ethylene glycol, 1,2-propanediol, 1,3-propanediol, 1,1-dimethylethane-1,2-diol, 2-butyl-2-ethyl-1,3-propanediol, 2-ethyl-1,3-propanediol, 2-methyl-1,3-propanediol, neopentyl glycol, neopentyl glycol hydroxypivalate, 1,2-, 1,3- or 1,4-butanediol, 1,6-hexanediol, 1,10-decanediol, bis(4-hydroxycyclohexane)isopropylidene, tetramethylcyclobutanediol, 1,2-, 1,3- or 1,4-cyclohexanediol, cyclooctanediol, norbornanediol, pinanediol, decalindiol, 2-ethyl-1,3-hexanediol, 2,4-diethyloctane-1,3-diol, hydroquinone, bisphenol A, bisphenol F, bisphenol B, bisphenol S, 2,2-bis(4-hydroxycyclohexyl)propane, 1,1-, 1,2-, 1,3- and 1,4-cyclohexanedimethanol, and 1,2-, 1,3- or 1,4-cyclohexanediol. These compounds may be prepared, for example, by reacting said diols with an excess of, for example, the above-recited carbonates RO(CO)OR or chlorocarbonic esters, so that the dicarbonates thus obtained are substituted on both sides by groups RO(CO)—. A further possibility is to react the diols first with phosgene to give the corresponding chlorocarbonic esters of the diols, and then to react these esters with alcohols.

Further compounds (A1) are dicarboxylic acids, esters of dicarboxylic acids, preferably the methyl, ethyl, isopropyl, n-propyl, n-butyl, isobutyl, sec-butyl or tert-butyl esters, more preferably the methyl, ethyl or n-butyl esters. Examples of dicarboxylic acids of this kind are oxalic acid, maleic acid, fumaric acid, succinic acid, glutaric acid, adipic acid, sebacic acid, dodecanedioic acid, o-phthalic acid, isophthalic acid, terephthalic acid, azelaic acid, 1,4-cyclohexanedicarboxylic acid or tetrahydrophthalic acid, suberic acid, phthalic anhydride, tetrahydrophthalic anhydride, hexahydrophthalic anhydride, tetrachlorophthalic anhydride, endomethylenetetrahydrophthalic anhydride, glutaric anhydride, dimeric fatty acids, isomers thereof and hydrogenation products thereof.

The simplest structure of the condensation product (K), illustrated using, as example, the reaction of a carbonate (A) with a dialcohol or polyalcohol (B), produces the arrangement $XY_m$ or $Y_mX$, X being a carbonate or carbamoyl group, Y a hydroxyl group, and m generally an integer greater than 1 to 6, preferably greater than 1 to 4, more preferably greater than 1 to 3. The reactive group, which results as a single group, is generally referred to below as "focal group".

Where, for example, in the preparation of the simplest condensation product (K) from a carbonate and a dihydric alcohol, the molar reaction ratio is 1:1, then the result on average is a molecule of type XY, illustrated by the general formula (I).

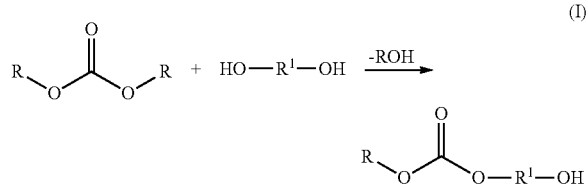

In the case of the preparation of the condensation product (K) from a carbonate and a trihydric alcohol with a molar reaction ratio of 1:1, the result on average is a molecule of type $XY_2$, illustrated by the general formula (II). The focal group here is a carbonate group.

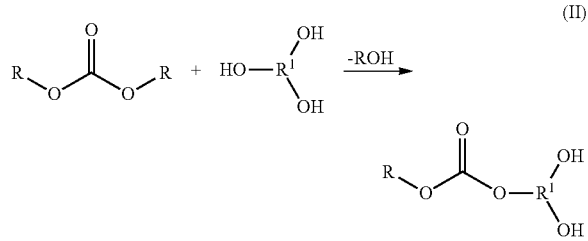

In the preparation of the condensation product (K) from a carbonate and a tetrahydric alcohol, again with the molar reaction ratio 1:1, the result on average is a molecule of type $XY_3$, illustrated by the general formula (III). The focal group here is a carbonate group.

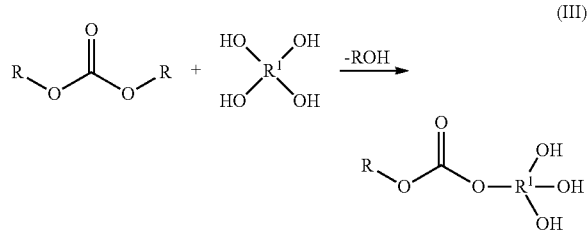

In the formulae (I) to (III) R is as defined at the outset and $R^1$ is an aliphatic or aromatic radical.

The condensation product (K) can also be prepared, for example, from a carbonate and a trihydric alcohol, illustrated by the general formula (IV), where the reaction ratio on a molar basis is 2:1. Here the result on average is a molecule of type $X_2Y$, the focal group here being an OH group. In the formula (IV) the definitions of R and $R^1$ are the same as above in formulae (I) to (III).

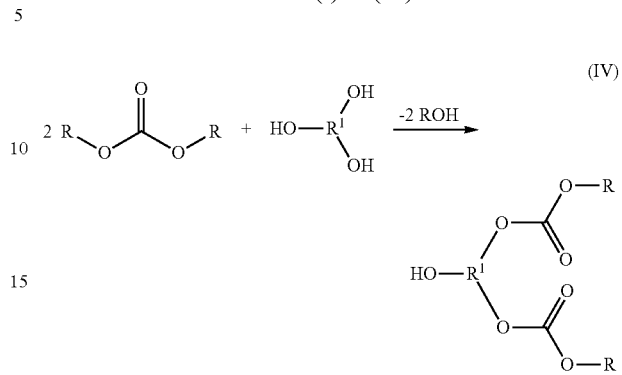

Where difunctional compounds, e.g., a dicarbonate or a diol, are additionally added to the components, this produces an extension of the chains, as illustrated for example in the general formula (V). The result again is on average a molecule of type $XY_2$, the focal group being a carbonate group.

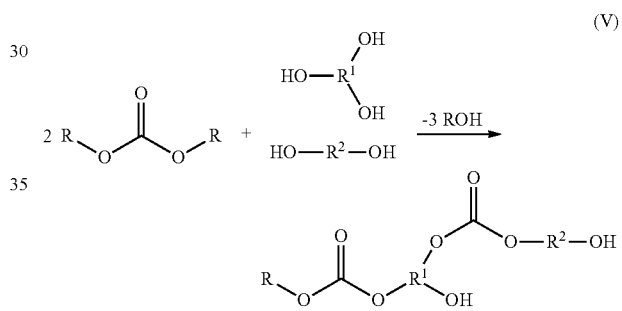

In formula (V) $R^2$ is an aliphatic or aromatic radical while R and $R^1$ are defined as described above.

It is also possible to use two or more condensation products (K) for the synthesis. In this case it is possible on the one hand to use two or more alcohols and/or two or more carbonates. Furthermore, through the choice of the ratio of the alcohols and carbonates or phosgenes used, it is possible to obtain mixtures of different condensation products with different structure. This may be exemplified taking, as example, the reaction of a carbonate with a trihydric alcohol. If the starting products are used in a 1:1 ratio, as depicted in (II), a molecule $XY_2$ is obtained. If the starting products are used in a 2:1 ratio, as illustrated in (IV), the result is a molecule $X_2Y$. With a ratio between 1:1 and 2:1 a mixture of molecules $XY_2$ and $X_2Y$ is obtained.

Typical reaction conditions for the reaction of (A) with (B) to form the condensation product (K) are set out below:

The stoichiometry of components (A) and (B) is generally chosen such that the resultant condensation product (K) contains either one carbonate or carbamoyl chloride group and more than one OH group, or one OH group and more than one carbonate or carbamoyl chloride group. This is achieved in the first case by a stoichiometry of 1 mol of carbonate groups: >2 mol of OH groups, for example, a stoichiometry of 1:2.1 to 8, preferably 1:2.2 to 6, more preferably 1:2.5 to 4, and very preferably 1:2.8 to 3.5. In the second case it is achieved by a stoichiometry of more than 1 mol of carbonate groups: <1 mol of OH groups, for example, a stoichiometry of 1:0.1 to 0.48, preferably 1:0.15 to 0.45, more preferably 1:0.25 to 0.4, and very preferably 1:0.28 to 0.35.

The temperature ought to be sufficient for the reaction of the alcohol with the corresponding carbonyl component. For the reaction with a phosgene a sufficient temperature is generally from −20° C. to 120° C., preferably 0 to 100° C., and more preferably 20 to 80° C. When a carbonate is used the temperature should be 60 to 280° C., preferably 80 to 250° C., more preferably 100 to 250° C., and very preferably 120 to 250° C.

Preparation takes place usually in a pressure range from 0.1 mbar to 20 bar, preferably at 1 mbar to 5 bar, in reactors or reactor cascades, which are operated batchwise, semi-batchwise or continuously.

Solvents contemplated include aromatic and/or (cyclo) aliphatic hydrocarbons and mixtures thereof, halogenated hydrocarbons, ketones, esters, and ethers, preferably butyl acetate, dimethylformamide, dimethylacetamide, dimethyl sulfoxide, methoxy-propyl acetate, isobutyl methyl ketone, 2-butanone, aromatic hydrocarbons (such as Solvesso® products), cyclohexane, chlorobenzene, and xylene. A preferred embodiment is to carry out the reaction without solvent.

The order in which the individual components are added is generally of minor importance. As a general rule it is sensible to introduce the excess component of the two reaction partners first and to add the deficit component. Alternatively it is likewise possible to mix the two components with one another before the beginning of reaction and then to heat this mixture to the requisite reaction temperature.

The simple condensation products (K) described exemplarily in formulae (I)-(V) undergo in accordance with the invention preferably immediate intermolecular further reaction to form high-functionality polycondensation products, referred to below as polycondensation products (P). The reaction to give the condensation product (K) and to give the polycondensation product (P) takes place usually at a temperature of 0 to 300° C., preferably 0 to 250° C., more preferably at 60 to 250° C., and very preferably at 80 to 250° C., in bulk (without solvent) or in solution. In this context it is possible generally to use any solvents which are inert toward the respective reactants. Preference is given to using organic solvents, such as those mentioned above, for example, and more preferably decane, dodecane, cyclohexane, benzene, toluene, chlorobenzene, xylene, dimethylformamide, dimethylacetamide, dimethyl sulfoxide or solvent naphtha. In one preferred embodiment the condensation reaction is carried out in bulk. The monofunctional alcohol or the phenol which is liberated during the reaction, ROH, can be removed from the reaction equilibrium in order to accelerate the reaction, such removal taking place, for example, by distillative means, if desired under reduced pressure.

The separation of the alcohol or phenol can also be assisted by passing through the reaction mixture a stream of gas which is substantially inert under the reaction conditions (i.e., stripping), such as, for example, nitrogen, steam, carbon dioxide, or else by passing through the mixture an oxygen-containing gas, such as atmospheric air or lean air, for example. If distillative removal is intended, it is advisable as a general rule to use carbonates which during the reaction give off alcohols or phenols ROH having a boiling point of less than 140° C. under the prevailing pressure.

Alternatively the alcohols liberated may be removed by azeotropic distillation using azeotrope formers (e.g., toluene, xylene, chlorobenzene, cyclohexane) or by application of a vacuum, such removal supporting the formation of the polycondensate.

To accelerate the reaction it is also possible to add catalysts or catalyst mixtures. Suitable catalysts are compounds which catalyze esterification or transesterification reactions, examples being alkali metal hydroxides, alkali metal carbonates, alkali metal hydrogen carbonates, preferably of sodium, of potassium or of cesium, tertiary amines, guanidines, ammonium compounds, phosphonium compounds, organoaluminum, organotin, organozinc, organotitanium, organozirconium or organobismuth compounds, and also catalysts of the kind known as double metal cyanide (DMC) catalysts, as described, for example, in DE 10138216 or in DE 10147712. Preference is given to using potassium hydroxide, potassium carbonate, potassium hydrogen carbonate, diazabicyclooctane (DABCO), diazabicyclononene (DBN), diazabicycloundecene (DBU), imidazoles, such as imidazole, 1-methylimidazole or 1,2-dimethylimidazole, titanium tetrabutoxide, titanium tetraisopropoxide, dibutyltin oxide, dibutyltin dilaurate, tin dioctoate, zirconium acetylacetonate, or mixtures thereof. The catalyst is generally added in an amount of 50 to 10 000 ppm by weight, preferably of 100 to 5000 ppm by weight, based on the amount of alcohol or alcohol mixture employed. It may possibly be necessary to predissolve the catalyst in small amounts of a suitable solvent.

Furthermore it is also possible, either by adding the appropriate catalyst and/or by choosing a suitable temperature, to control the intermolecular polycondensation reaction. In addition the average molecular weight of the polymer (P) can be adjusted via the composition of the starting components and via the residence time.

The condensation products (K) and the polycondensation products (P), which have been prepared at an elevated temperature, are stable at room temperature usually for a relatively long period of time, for example, for at least 6 weeks, without displaying turbidities, precipitations and/or any increase in viscosity. In view of the nature of the condensation products (K) it is possible that the condensation reaction may result in polycondensation products (P) having different structures, with branches but no crosslinks. Furthermore, the polycondensation products (P) ideally contain either a carbonate or carbamoyl chloride focal group and more than two OH groups, or else an OH focal group and more than two carbonate or carbamoyl chloride groups. The number of reactive groups depends on the nature of the condensation products (K) employed and on the degree of polycondensation.

For example, a condensation product (K) of the general formula (II) may react by triple intermolecular condensation to form two different polycondensation products (P), which are reproduced in general formulae (VI) and (VII).

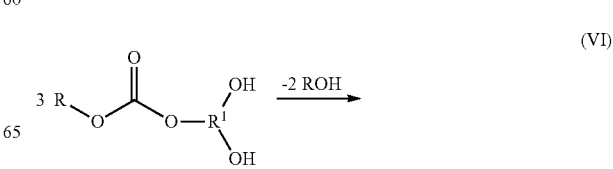

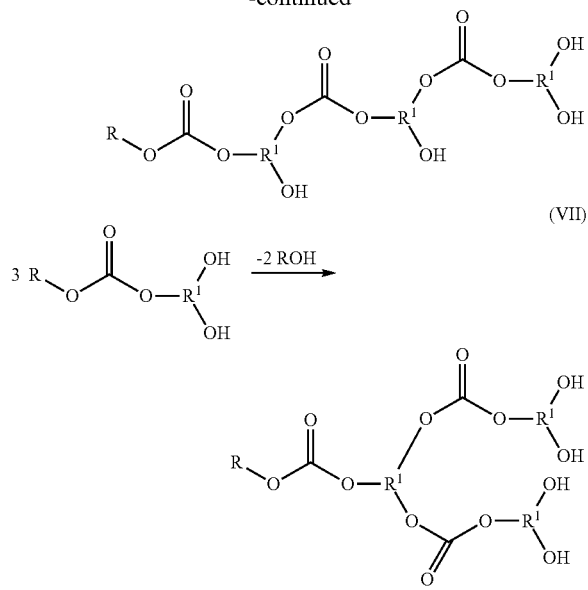

R and R¹ in formulae (VI) and (VII) are as defined above.

To terminate the intermolecular polycondensation reaction there are a variety of possibilities. By way of example the temperature can be lowered to a range in which the reaction comes to a standstill and the product (K) or the polycondensation product (P) is stable on storage. This is generally the case at below 60° C., preferably below 50° C., more preferably below 40° C., and very preferably at room temperature. Furthermore, the catalyst can be deactivated: in the case of basic catalysts, for example, by adding an acidic component, a Lewis acid for example, or an organic or inorganic protic acid. A further possibility is to arrest the reaction by dilution with a precooled solvent. This is particularly preferred when it is necessary to adapt the viscosity of the reaction mixture by adding solvent.

In a further embodiment, as soon as the intermolecular reaction of the condensation product (K) gives a polycondensation product (P) having the desired degree of polycondensation, the reaction can be arrested by adding to the product (P) a product having groups that are reactive toward the focal group of (P). For instance, in the case of a carbonate or carbamoyl focal group, a mono-, di- or polyamine, for example, can be added. In the case of a hydroxyl focal group, the product (P) can have added to it, for example, a mono-, di- or polyisocyanate, a compound comprising epoxide groups, or an acid derivative which is reactive with OH groups.

As a result of the aforementioned setting of the reaction conditions and, if desired, as a result of the choice of suitable solvent, the products of the invention can be processed further following preparation, without additional purification. If necessary, the reaction mixture can be subjected to decoloring, by means for example of treatment with activated carbon or metal oxides, such as alumina, silica, magnesium oxide, zirconium oxide, boron oxide or mixtures thereof, in amounts for example of 0.1%-50%, preferably 0.5% to 25%, more preferably 1%-10%, by weight, at temperatures of, for example, 10 to 100° C., preferably 20 to 80° C., and more preferably 30 to 60° C. If desired it is also possible to filter the reaction mixture in order to remove any precipitates present. In a further preferred embodiment the product is stripped, i.e., freed from volatile compounds of low molecular weight. For this purpose, after the desired degree of conversion has been reached, the catalyst can be optionally deactivated and the volatile constituents of low molecular weight, such as monoalcohols, phenols, carbonates, hydrogen chloride or volatile oligomeric or cyclic compounds, can be removed by distillation, if desired accompanied by introduction of a gas, preferably nitrogen, carbon dioxide or air, if desired under reduced pressure.

The hyperbranched polycarbonates obtainable as described above generally have a glass transition temperature of less than 50° C., preferably less than 30 and more preferably less than 10° C. The OH number is usually at least 30 mg KOH/g, preferably between 50 and 250 mg/g. The weight-average molar weight $M_w$ is usually between 1000 and 150 000, preferably from 1500 to 100 000 g/mol, the number-average molar weight $M_n$ between 500 and 50 000, preferably between 1000 and 40 000 g/mol. The hyperbranched polycarbonate is usually not soluble or dispersible in water, i.e., it is not possible to prepare a clear (i.e., devoid of particles visible to the naked eye) aqueous solution or dispersion.

The amphiphile preferably comprises a hyperbranched polycarbonate which is joined to at least one linear or comb-type polymer and/or to at least one functional $C_1$-$C_{24}$ unit comprising an acid group, an amino group or at least two hydroxyl groups. With particular preference the amphiphile comprises a hyperbranched polycarbonate which is joined to at least one linear or comb-type polymer or to at least one functional $C_1$-$C_{24}$ unit comprising an acid group, an amino group or at least two hydroxyl groups. With very particular preference the amphiphile comprises a hyperbranched polycarbonate which is joined to at least one linear or comb-type polymer. The molar ratio of hyperbranched polycarbonate to the sum of linear or comb-type polymer and of functional $C_1$-$C_{24}$ unit is usually in the range from 1:1 to 1:100, preferably 1:1 to 1:50, more preferably 1:1 to 1:25.

The composition of the invention usually comprises 0.01% to 40%, preferably 0.05% to 30%, more preferably from 0.1% to 20% by weight of amphiphile. The amphiphile is usually soluble or dispersible in water, i.e., it is possible to prepare a clear (i.e., devoid of particles visible to the naked eye) aqueous solution or dispersion.

In one preferred embodiment the amphiphile comprises a hyperbranched polycarbonate which is joined to at least one linear or comb-type polymer. The linkage is usually by means of a linker.

The linear polymer is preferably
a) a homopolymer or random copolymer comprising a polar ethylenically unsaturated monomer,
b) a block polymer comprising a block of polyethylene glycol or based on at least one polar ethylenically unsaturated monomer, or
c) a polycondensate comprising polyethylene glycol, or
d) a polyethylene glycol, the polyethylene glycol d) being joined to the polycarbonate via a linker. The linear polymer is more preferably one of the aforementioned polymers a), b) or c). In a further particularly preferred embodiment, the linear polymer is one of the aforementioned polymers a), c) or d). The linear polymer is especially preferably one of the aforementioned polymers a) or c), especially a).

In one embodiment, the linear polymer may be a homopolymer or random copolymer comprising a polar ethylenically unsaturated monomer. The number-average molar mass $M_n$ is usually less than 100 000 g/mol, preferably less than 50 000 g/mol, more preferably less than 20 000 g/mol and most preferably less than 10 000 g/mol, and can be determined by means of GPC and a suitable standard. $M_n$ is typically more than 200 g/mol, preferably more than 500 g/mol.

Suitable polar ethylenically unsaturated monomers are monomers which bear charge or bear ionizable groups and comprise a polymerizable ethylenically unsaturated bond. Examples of charge-bearing or ionizable groups are carboxylic acid, sulfonic acid, polyethylene glycol, alcohol, nitrile, amide, amine, dialkylamine. Examples of polar ethylenically unsaturated monomers are vinylpyrrolidone, (meth)acrylic acid, a sulfo-containing (meth)acrylate (such as 2-acrylamido-2-methylpropanesulfonic acid), an aminofunctional (meth)acrylate (such as dimethylaminoethyl (meth)acrylate), (meth)acrylic esters of a polyethylene glycol derivative (such as polyethylene glycol monomethyl ether (meth)acrylate), itaconic acid, maleic anhydride, $C_1$-$C_{20}$-alkyl (meth)acrylates substituted by OH groups (such as hydroxyethyl(meth)acrylate, hydroxybutyl(meth)acrylate), (meth)acrylonitrile, (meth)acrylamide, N-methylol (meth)acrylamide. Preferred polar ethylenically unsaturated monomers are vinylpyrrolidone, (meth)acrylic acid, polyethylene glycol monomethyl ether (meth)acrylate, polyethylene glycol (meth)acrylate. The expression "(meth)acrylic" means "acrylic" or "methacrylic".

Examples of linear homopolymers comprising a polar ethylenically unsaturated monomer are homopolymers of the aforementioned polar ethylenically unsaturated monomers, preferably of vinylpyrrolidone, (meth)acrylic acid, polyethylene glycol monomethyl ether (meth)acrylate, polyethylene glycol (meth)acrylate.

Examples of random copolymers comprising a polar ethylenically unsaturated monomer are copolymers of the aforementioned polar ethylenically unsaturated monomers, preferably of vinylpyrrolidone, (meth)acrylic acid, polyethylene glycol monomethyl ether (meth)acrylate, polyethylene glycol (meth)acrylate. As further monomer, the random copolymer may comprise: esters of acrylic acid with $C_1$-$C_{10}$-alkanols such as ethyl acrylate, n-butyl acrylate, isobutyl acrylate, tert-butyl acrylate, n-hexyl acrylate, 2-ethylhexyl acrylate and 3-propylheptyl acrylate, the esters of methacrylic acid with $C_1$-$C_{10}$-alkanols such as methyl methacrylate, ethyl methacrylate, n-butyl methacrylate, isobutyl methacrylate, tert-butyl methacrylate and n-hexyl methacrylate, N—($C_2$-$C_{10}$-alkyl)amides of acrylic acid and of methacrylic acid, and the N—($C_1$-$C_2$-alkyl)-N—($C_2$-$C_{10}$-alkyl) amides of acrylic acid and of methacrylic acid, e.g. N-ethylacrylamide, N,N-diethylacrylamide, N-butylacrylamide, N-methyl-N-propylacrylamide, N-(n-hexyl)acrylamide, N-(n-octyl)acrylamide and the corresponding methacrylamides, vinylaromatic monomers such as styrene, methylstyrene, vinyltoluene, olefins having 2 to 10 carbon atoms, preferably α-olefins having 3 to 10 carbon atoms, such as propene, 1-butene, 1-pentene, 1-hexene, 1-octene and 1-decene, vinyl esters of aliphatic carboxylic acids such as vinyl acetate, vinyl propionate, vinyl laurate, vinyl nonanoate, vinyl decanoate, vinyl laurate and vinyl stearate, unsaturated nitriles such as acrylonitrile and methacrylonitrile, halogenated olefins such as vinyl chloride, $C_{11}$-$C_{20}$-alkyl esters of monoethylenically unsaturated monocarboxylic acids having preferably 3 to 6 carbon atoms, e.g. $C_{11}$-$C_{20}$-alkyl acrylates and $C_{11}$-$C_{20}$-alkyl methacrylates such as lauryl acrylate, lauryl methacrylate, isotridecyl acrylate, isotridecyl methacrylate, stearyl acrylate, stearyl methacrylate, di-$C_1$-$C_{20}$-alkyl esters of ethylenically unsaturated dicarboxylic acids having preferably 4 to 8 carbon atoms, e.g. di-$C_1$-$C_{20}$-alkyl esters of fumaric acid and of maleic acid such as dimethyl fumarate, dimethyl maleate, dibutyl fumarate and dibutyl maleate, glycidyl esters of monoethylenically unsaturated monocarboxylic acids having preferably 3 to 6 carbon atoms, such as glycidyl acrylate and glycidyl methacrylate. Preferred further monomers are the esters with $C_1$-$C_{10}$-alkanols of acrylic acid and of methacrylic acid.

In a further embodiment, the linear polymer may be a block polymer comprising a block of polyethylene glycol or of at least one polar ethylenically unsaturated monomer. The molar mass $M_n$ is usually in the range of 200-10 000 g/mol, preferably between 300 and 2000 g/mol, and can be determined by GPC. The block polymer may be of the A-B or A-B-A type, preferably A-B type. The preparation of block polymers of these types is common knowledge. Suitable and preferred polar ethylenically unsaturated monomers are as specified above. Examples of a block of polyethylene glycol are polyethylene glycol or polyethylene glycol monoalkyl ethers having a molar mass $M_n$ of 200 to 10 000 g/mol. Examples of a block of at least one polar ethylenically unsaturated monomer are polyvinylpyrrolidone or poly(meth)acrylic acid or polyethylene glycol monomethyl ether (meth)acrylate. The other block in each case may be formed from polymer blocks from the prior art. The other block is preferably nonpolar; for example, it is formed from caprolactone or propylene oxide. In a further embodiment, the other block comprises polyesters (for example based on a dicarboxylic acid and a diol), polyamide (for example based on a dicarboxylic acid and a diamine), polycarbonate, polyurethane or polyurea. Preferred block polymers are polyethylene glycol-block-polycaprolactone and polyethylene glycol monomethyl ether-block-polycaprolactone and polypropylene glycol-block-polyethylene glycol.

In a further embodiment, the linear polymer may be a polycondensate comprising polyethylene glycol. In the context of the present invention, the term "polycondensate" also includes polyaddition products. Examples of polyethylene glycol are polyethylene glycol or polyethylene glycol monoalkyl ethers having a molar mass $M_n$ of 200 to 10 000 g/mol. Examples of polycondensates are polyethers, polyamides, polyimides, polyesters, polycarbonates, polyurethanes and polyureas, preferably polyethers and polyesters. A preferred polycondensate is a polyether based on $C_3$-$C_{24}$ alkylene oxide, particularly propylene oxide, and a polyester based on hydroxycarboxylic acid compounds, dialcohol compounds or diacid compounds, particularly hydroxycarboxylic acid compounds. Preferred hydroxycarboxylic acid compounds are lactones, especially $C_4$ to $C_{18}$-alkyl lactones, most preferably ε-caprolactone.

In a further embodiment, the linear polymer may be a polyethylene glycol, in which case the polyethylene glycol is joined to the polycarbonate via a linker. The linker is preferably a polyisocyanate. Examples of polyethylene glycol are polyethylene glycol or polyethylene glycol monoalkyl ethers having a molar mass $M_n$ of 200 to 10 000 g/mol, preferably 300-2000 g/mol. The polyethylene glycol is preferably a polyethylene glycol mono-$C_1$-$C_{18}$-alkyl ether, especially a polyethylene glycol monomethyl ether.

Comb-type polymers are understood here to mean comb polymers which typically comprise relatively long side chains of virtually equal length, preferably aliphatic side chains, at more or less regular intervals on a linear main chain. The molar mass $M_n$ is usually in the range from 500 to 100 000 g/mol and can be determined by GPC. The comb-type polymer preferably comprises polyalkylene glycol mono(meth)acrylate or allyl alcohol alkoxylate (such as polyethylene glycol allyl ether) in polymerized form, preferably polyethylene glycol monoalkyl ether (meth)acrylate with a molar mass $M_n$ of 100 to 5000 g/mol. The comb polymer more preferably comprises polyethylene glycol monomethyl ether acrylate or polyethylene glycol monomethyl ether methacrylate with a molar mass $M_n$ of in each case 100 to 3000 g/mol, preferably 200 to 1500 g/mol. In addition to polyalkylene glycol mono(meth)acrylate or allyl alcohol alkoxylates, the comb polymer may comprise any desired copolymerizable ethylenically unsaturated monomers. Preferred additional monomers are nonpolar monomers and/or the aforementioned polar ethylenically unsaturated monomers. Preferred nonpolar monomers are $C_1$-$C_{20}$-alkyl(meth)acrylates or vinylaromatics having up to 20 carbon atoms. Examples comprise methyl(meth)acrylate, ethyl(meth)acrylate, n-butyl (meth)acrylate, 2-ethylhexyl (meth)acrylate, lauryl(meth)acrylate or 4-t-butylcyclohexyl (meth)acrylate. Useful vinylaromatic compounds include, for example, vinyltoluene, α-butylstyrene, 4-n-butylstyrene, 4-n-decylstyrene or styrene. Preferred additional monomers are methyl(meth)acrylate, lauryl acrylate, stearyl acrylate, styrene, vinylpyrrolidone or mixtures thereof.

The linear or comb-type polymer can be prepared by commonly known methods (for example from U.S. Pat. No. 5,556,918 and EP-A 742 238). In one embodiment, the linear polymer, which is a homopolymer or random copolymer comprising a polar ethylenically unsaturated monomer, the block polymer comprising a block of polyethylene glycol or based on at least one polar ethylenically unsaturated monomer, and the comb polymer, are prepared by free-radically initiated solution polymerization of the monomers in the presence of an initiator and if appropriate of a regulator. Preference is given to using an initiator which, when it decomposes, forms a hydroxyl radical (OH radical), and/or a regulator which comprises an OH group or an $NH_2$ group. These OH or $NH_2$ groups can be used later as the linker-reactive group.

Suitable initiators are organic hydroperoxides such as tert-butyl hydroperoxide, tetrahydrofuran hydroperoxide, cumene hydroperoxide or 2,2'-azobis(2-methyl-N-(2-hydroxyethyl)propionamide). Suitable regulators are aminoalcohols, aminophenols and especially thioalkanols such as 3-hydroxypropanethiol, 3-mercapto-1,2-propanediol, 2-hydroxyethyl 3-mercaptopropionate, and in particular 2-hydroxyethanethiol (mercaptoethanol). When such a regulator is used, the polymerization can also be performed in the presence of a conventional initiator, for example of a conventional azo initiator or of an organic peroxide such as azobis(isobutyronitrile), di-(tert-butyl) peroxide, didecanoyl peroxide, dibenzoyl peroxide, tert-butyl peracetate or tert-butyl 2-methylperpropionate. When the polymerization is performed in the presence of one of the aforementioned regulators, the regulator will generally be used in an amount of 0.1 to 12% by weight, frequently 0.2 to 8% by weight and especially 0.5 to 5% by weight, based on the total amount of the monomers. Initiators are generally used in an amount of 0.05 to 5% by weight, frequently 0.1 to 4% by weight and more preferably in an amount of 0.2 to 3% by weight, based on the monomers to be polymerized. For further details, reference is made especially to page 3 of EP 742 238, whose disclosure is incorporated by reference.

In a further preferred embodiment, the amphiphile comprises a hyperbranched polycarbonate which is joined to at least one functional $C_1$-$C_{24}$ unit comprising an acid group, an amino group or at least two hydroxyl groups. The functional $C_1$-$C_{24}$ unit preferably comprises a carboxylic acid group, a sulfonic acid group, a sulfenic acid group, a sulfinic acid group, a sulfuric ester group (i.e. an organic sulfate), a phosphonic acid group, an amino group or at least two hydroxy-$C_2$-$C_{10}$-alkyl groups, more preferably a carboxylic acid group. Optionally, the functional $C_1$-$C_{24}$ unit may also comprise a plurality of the groups listed at the same time.

In one embodiment, the functional $C_1$-$C_{24}$ unit additionally comprises a joining group with which the functional $C_1$-$C_{24}$ unit can be joined covalently to the hyperbranched polycarbonate, directly or by means of a linker. Suitable joining groups may react with the OH and/or carbonate or carbamoyl chloride groups of the polycarbonate. Examples are carboxylic acids, carboxylic esters, carboxylic anhydrides, isocyanates, amines and alcohols. Further suitable joining groups may react with the linker. Examples are alcohols or amines, preferably alcohols. Suitable linkers are described hereinafter.

The hyperbranched polycarbonate which is linked to the functional $C_1$-$C_{24}$ unit is usually obtainable and preferably obtained by reacting the hyperbranched polycarbonate with a functionalizing reagent which comprises the functional $C_1$-$C_{24}$ unit comprising an acid group, an amino group or at least two hydroxyl groups and the joining group, and optionally with a linker.

Suitable functionalizing reagents for direct covalent joining without a linker are anhydrides. Particularly suitable are cyclic carboxylic anhydrides, such as succinic anhydride or phthalic anhydride, especially succinic anhydride. Typically, the anhydrides are reacted with the hyperbranched polycarbonate at elevated temperatures, usually at 80 to 200° C. The reaction can be effected with or without addition of solvents. Further purification is normally not necessary.

Suitable functionalizing reagents for covalent joining by means of a linker are hydroxycarboxylic acids, aminocarboxylic acids, hydroxysulfonic acids, hydroxysulfates, aminosulfonic acids or aminosulfates, hydroxylamines (such as diethanolamine), polyamines (e.g. diethylenetetramine) or polyols (e.g. glycerol, trimethylolpropane, pentaerythritol). Preferred linkers for this purpose are polyisocyanates described below, preferably diisocyanates, more preferably aliphatic diisocyanates (such as hexamethylene diisocyanate and isophorone diisocyanate).

The linear or comb-type polymers are preferably joined to the hyperbranched polycarbonate with the aid of a linker. Usually, the linker is first bonded covalently to the linear or comb-type polymer, in order then to couple the linker-containing polymer onto the hyperbranched polycarbonate. In order that the linker-containing polymer can be prepared, the starting polymer usually comprises a group which can react with the linker (linker-reactive group). The mean number of linker-reactive groups is generally not more than two, and is preferably in the range from 0.3 to 1.8, in particular in the range from 0.5 to 1.5 and especially in the range from 0.6 to 1.4 per polymer molecule. The linker-reactive group may be arranged within the polymer chain or is preferably at the end of the polymer chain.

In the case of a linear polymer which is a homopolymer or random copolymer comprising a polar ethylenically unsaturated monomer, a block polymer comprising a block of polyethylene glycol or based on at least one polar ethylenically unsaturated monomer, or of a comb polymer, the linker-reactive group can be introduced as described above by means of a suitable initiator and/or regulator. Alternatively, the linker-reactive group can be introduced at the chain end in a controlled manner by means of a controlled free-radical reaction according to the prior art (such as Atom Transfer Radical Polymerization (ATRP), Reversible Addition Fragmentation Chain Transfer Polymerization (RAFT), or Nitroxide Mediated Polymerization (NMP)). It is equally possible that a functional group in the polymer chain is used as the linker-reactive group, for example one of possibly several OH groups of a polymerized hydroxyethyl(meth)acrylate.

In the case of a polycondensate comprising polyethylene glycol, a linker-reactive group can be obtained at the chain end of the polycondensate by means of a suitable stoichiometry and use of a monofunctional monomer. The linker-reactive group is preferably obtained by ring-opening polymerization of a lactone, such that exactly one functional hydroxyl group forms at the chain end.

In the case of a polyethylene glycol, the linker-reactive group used may be a hydroxyl group at the chain end. Preference is given to polyethylene glycol monoalkyl ethers which have exactly one linker-reactive group at the chain end.

In general, useful linkers include reactive polyfunctional compounds with at least two reactive groups. Preferred linkers are polyisocyanates having a functionality based on the isocyanate groups of at least 1.5, in particular 1.5 to 4.5 and especially 1.8 to 3.5, comprise aliphatic, cycloaliphatic and aromatic di- and polyisocyanates, and the isocyanurates, allophanates, uretdiones and biurets of aliphatic, cycloaliphatic and aromatic diisocyanates. The polyisocyanates preferably have an average of 1.8 to 3.5 isocyanate groups per molecule. Examples of suitable polyisocyanates are aromatic diisocyanates such as toluene 2,4-diisocyanate, toluene 2,6-diisocyanate, commercially available mixtures of toluene 2,4- and 2,6-diisocyanate (TDI), n-phenylene diisocyanate, 3,3'-diphenyl-4,4'-biphenylene diisocyanate, 4,4'-biphenylene diisocyanate, 4,4'-diphenylmethane diisocyanate, 2,4'-diphenylmethane diisocyanate, 3,3'-dichloro-4,4'-biphenylene diisocyanate, cumene 2,4-diisocyanate, 1,5-naphthalene diisocyanate, p-xylylene diisocyanate, p-phenylene diisocyanate, 4-methoxy-1,3-phenylene diisocyanate, 4-chloro-1,3-phenylene diisocyanate, 4-ethoxy-1,3-phenylene diisocyanate, 2,4-dimethylene-1,3-phenylene diisocyanate, 5,6-dimethyl-1,3-phenylene diisocyanate, 2,4-diisocyanatodiphenyl ether, aliphatic diisocyanates such as ethylene diisocyanate, ethylidene diisocyanate, propylene 1,2-diisocyanate, 1,6-hexamethylene diisocyanate (HDI), 1,4-tetramethylene diisocyanate, 1,10-decamethylene diisocyanate, and cycloaliphatic diisocyanates such as isophorone diisocyanate (IPDI), cyclohexylene 1,2-diisocyanate, cyclohexylene 1,4-diisocyanate and bis(4,4'-isocyanatocyclohexyl)methane. Among the polyisocyanates, preference is given to those whose isocyanate groups are of different reactivity, such as toluene 2,4-diisocyanate, toluene 2,6-diisocyanate, 2,4'-diphenylmethane diisocyanate, cis- and trans-isophorone diisocyanate, or mixtures of these compounds.

The reaction with the polyisocyanate is effected in the melt or in an organic solvent, preferably in an aprotic polar organic solvent or mixtures of such solvents. Examples are ketones (for example acetone), butyl acetate, tetrahydrofuran (THF), xylene, chlorobenzene, dimethyl sulfoxide (DMSO) or dimethylformamide (DMF). Preferred solvents are butyl acetate, xylene and acetone. The reaction is effected typically at elevated temperatures, the temperature also being guided by the boiling temperature of the solvent selected. The polyisocyanate can be reacted with the first component at 20 to 80° C., but if desired also to 100° C. The further isocyanate group can be reacted at temperatures of 50 to 100° C.

The reaction can be effected in an equimolar manner, which means that the quantitative ratio is selected such that 1 mol of diisocyanate is used per mole of hydroxyl group to be converted in the functionalizing reagent or in the linear or comb-type polymer. Preference is given to working with a slight (e.g. 0 to 15 mol %) excess of the hydroxyl groups, in order to reduce the amount of unconverted diisocyanate. When the free-radical copolymer is OH-functionalized by means of an initiator or regulator, the diisocyanate is reacted in an equimolar amount or in a slight deficiency relative to the OH groups introduced in this way. In the case of symmetric diisocyanates (such as HDI), it may also be advisable to use an excess of diisocyanate and then to remove the excess by distillation.

Preference is given to performing the reaction in the presence of a catalyst. Suitable catalysts are, for example, tertiary amines, for example triethylamine, tri-n-propylamine, N-methylpyrrolidine, N-methylpiperidine and diazabicyclooctane (DABCO), zinc carboxylates, bismuth carboxylates, titanium alkoxides, organotin compounds, especially dialkyltin(IV) salts of aliphatic carboxylic acids such as dibutyltin dilaurate and dibutyltin dioctoate, tin(II) dialkanoates such as tin dioctoate, and cesium salts such as cesium acetate. In one embodiment, zinc carboxylates, bismuth carboxylates, titanium alkoxides are particularly suitable, the carboxylates preferably being $C_1$-$C_{20}$ carboxylates (such as formate, acetate, propionate, hexanoate, octanoate or neodecanoate). The catalyst can be used in amounts of 50 to 50 000 ppm, preferably 100 to 5000 ppm, based on the overall solids.

The reaction is typically performed at elevated temperatures in the range from 40 to 120° C. Which temperature is selected in the individual case depends on the type of organic solvent used. The solvent can subsequently be removed by distillation.

Typically, the reaction will be performed in such a way that the component which is to be functionalized with isocyanate groups (for example the linear or comb-type polymer or the functional $C_1$-$C_{24}$ unit) is first reacted with the diisocyanate in the presence of the catalyst and of a solvent until the isocyanate value in the reaction mixture has fallen by half. In the case of use of a slight hydroxyl group excess, reaction is continued until the theoretical end value corresponds to the complete conversion of the hydroxyl groups. This can be determined, for example, by titrimetric means in a known manner. This is then followed by the addition of the other component (for example hyperbranched polycarbonate). The molar ratio of hyperbranched polycarbonate to linear polymer, comb-type polymer, or to the functional $C_1$-$C_{24}$ unit is 1:1 to 1:25, preferably 1:2 to 1:15. The reaction is continued until the isocyanate value has fallen to zero.

The composition of the invention is obtainable by bringing the amphiphile and the active ingredient whose solubility in water at 20° C. is not more than 10 g/L into contact, the amphiphile comprising a hyperbranched polycarbonate which is joined to at least one linear or comb-type polymer or to at least one functional $C_1$-$C_{24}$ unit comprising an acid group, an amino group or at least two hydroxyl groups. The components can be brought into contact by methods which are common knowledge, such as mixing, emulsifying or suspending.

The weight ratio of active ingredient to amphiphile is usually in the range from 100:1 to 1:100, preferably 10:1 to 1:50, more preferably 2:1 to 1:25. The active ingredient may be in dissolved form or in solid, particulate form. The active ingredient particles may be crystalline or amorphous. The particle size may be 1 nm to 10 μm. The composition may be a solution, emulsion, suspension or suspoemulsion of the active ingredient. The composition of the invention is preferably an aqueous composition. Preferably it comprises at least 40%, more preferably at least 60%, and more particularly at least 80% by weight of water. The composition typically comprises not more than 99% by weight of water.

The composition of the invention may comprise formulating assistants, the choice of assistants being guided typically by the specific application form and/or active ingredient. Examples of suitable formulating assistants are solvents, solid carriers, surface-active substances (such as surfactants, protective colloids, wetting agents, and stickers), organic and inorganic thickeners, bactericides, antifreeze agents, defoamers, colorants if desired, and adhesives (e.g., for seed treatment).

Surface-active substances contemplated (adjuvants, wetting agents, stickers, dispersants or emulsifiers) include the alkali metal, alkaline earth metal, and ammonium salts of aromatic sulfonic acids, e.g., those of lignosulfonic (Borresperse® products, Borregaard, Norway), phenolsulfonic, naphthalenesulfonic (Morwet® products, Akzo Nobel, USA), and dibutylnaphthalenesulfonic (Nekal® products, BASF, Germany) acid, and also of fatty acids, alkyl- and alkylarylsulfonates, alkyl, lauryl ether, and fatty alcohol sulfates, and also salts of sulfated hexa, hepta-, and octadecanols and also of fatty alcohol glycol ethers, condensation products of sulfonated naphthalene and its derivatives with formaldehyde, condensation products of naphthalene or of naphthalenesulfonic acids with phenol and formaldehyde, polyoxyethylene octylphenol ethers, ethoxylated isooctylphenol, octylphenol or nonylphenol, alkyllphenyl and tributylphenyl polyglycol ethers, alkylaryl polyether alcohols, isotridecyl alcohol, fatty alcohol ethylene oxide condensates, ethoxylated castor oil, polyoxyethylene or polyoxypropylene alkyl ethers, lauryl alcohol polyglycol ether acetate, sorbitol esters, lignin-sulfite waste liquors, and also proteins, denatured proteins, polysaccharides (e.g., methylcellulose), hydrophobically modified starches, polyvinyl alcohol (Mowiol® products, Clariant, Switzerland), polycarboxylates (Sokalan® products, BASF, Germany), polyalkoxylates, polyvinylamine (Lupamin® products, BASF, Germany), polyethyleneimine (Lupasol® products, BASF, Germany), polyvinylpyrrolidone and copolymers thereof.

Suitable surfactants include, in particular, anionic, cationic, nonionic, and amphoteric surfactants, block polymers, and polyelectrolytes. Suitable anionic surfactants are alkali metal, alkaline earth metal or ammonium salts of sulfonates, sulfates, phosphates or carboxylates. Examples of sulfonates are alkylarylsulfonates, diphenylsulphonates, alpha-olefinsulfonates, sulfonates of fatty acids and oils, sulfonates of ethoxylated alkylphenols, sulfonates of condensed naphthalenes, sulfonates of dodecyl and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates and carboxylated alcohol or alkylphenol ethoxylates.

Suitable nonionic surfactants are alkoxylates, N-alkylated fatty acid amides, amine oxides, esters or sugar-based surfactants. Examples of alkoxylates are compounds, such as alcohols, alkylphenols, amines, amides, arylphenols, fatty acids or fatty acid esters, which have been alkoxylated. For the alkoxylation it is possible to use ethylene oxide and/or propylene oxide, preferably ethylene oxide. Examples of N-alkylated fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose esters and glucose esters, or alkylpolyglucosides. Suitable cationic surfactants are quaternary surfactants, examples being quaternary ammonium compounds having one or two hydrophobic groups, or salts of long-chain primary amines. Suitable amphoteric surfactants are alkylbetaines and imidazolines. Suitable block polymers are block polymers of A-B or A-B-A type, comprising blocks of polyethylene oxide and polypropylene oxide, or of A-B-C type, comprising alkanol, polyethylene oxide, and polypropylene oxide. Suitable polyelectrolytes are polyacids or polybases. Examples of polyacids are alkali metal salts of polyacrylic acid. Examples of polybases are polyvinylamines or polyethylenamines.

The composition of the invention may comprise large amounts of surface-active substances and surfactant. It may comprise 0.1% to 40%, preferably 1% to 30% and more particularly 2% to 20% by weight in total amount of surface-active substances and surfactants, based on the total amount of the composition.

Examples of adjuvants are organically modified polysiloxanes, such as BreakThruS 240®; alcohol alkoxylates, such as Atplus®245, Atplus®MBA 1303, Plurafac®LF, and Lutensol® ON; EO-PO block polymers, e.g., Pluronic® RPE 2035 and Genapol® B; alcohol ethoxylates, e.g., Lutensol® XP 80; and sodium dioctylsulfosuccinate, e.g., Leophen® RA.

Examples of thickeners (i.e., compounds which give the composition a modified rheology, i.e., high viscosity in the state of rest and low viscosity in the mobile state) are polysaccharides and also organic and inorganic layer minerals such as xanthan gum (Kelzan®, CP Kelco), Rhodopol® 23 (Rhodia) or Veegum® (R.T. Vanderbilt) or Attaclay® (Engelhard Corp.).

In one preferred embodiment the active compound is a pesticide and the compositions of the invention are in the form of an agrochemical formulation. Suitable agrochemical formulations are water-soluble concentrates (SL, LS), redispersible concentrates (DC), emulsifiable concentrates (EC), emulsions (EW, EO, ES, ME), suspensions (SC, OD, FS) or suspoemulsions (SE). The composition preferably takes the form of an emulsifiable concentrate (EC), a suspension concentrate (SC), a water-soluble concentrate (SL), a solution for seed treatment (LS), or a redispersible concentrate (DC).

The agrochemical formulation is usually diluted prior to application, to prepare what is known as a tankmix. Suitable agents for the dilution include mineral oil fractions of moderate to high boiling point, such as kerosene or diesel oil, and also coal tar oils and oils of vegetable or animal origin, aliphatic, cyclic, and aromatic hydrocarbons, e.g., toluene, xylene, paraffin, tetrahydronaphthalene, alkylated naphthalenes or derivatives thereof, methanol, ethanol, propanol, butanol, cyclohexanol, cyclohexanone, isophorone, strongly polar solvents, e.g., dimethyl sulfoxide, N-methylpyrrolidone or water. It is preferred to use water. It is also possible to add the amphiphile only to the actual tankmix. In this embodiment the composition of the invention is in the form of a tankmix.

The diluted composition is typically applied by spraying or nebulizing. To the tankmix it is possible to add oils of various types, wetting agents, adjuvants, herbicides, bactericides or fungicides immediately prior to application (tankmix). These agents may be admixed to the compositions of the invention in a weight ratio of 1:100 to 100:1, preferably 1:10 to 10:1. The concentration of pesticide in the tankmix may be varied within relatively wide ranges. Concentrations are in general between 0.0001% and 10%, preferably between 0.01% and 1%. In the case of application in crop protection, and depending on the nature of the desired effect, the application rates are between 0.01 and 2.0 kg of active ingredient per ha.

The agrochemical formulations can be used to control phytopathogenic fungi and/or unwanted plant growth and/or unwanted insect or mite infestation and/or to regulate the growth of plants, the composition then being caused to act on the respective pests, their habitat, or the plants to be protected from the respective pest, the soil, and/or on unwanted plants and/or on the crop plants and/or on their habitat.

The agrochemical formulations can also be used to control unwanted insect or mite infestation on plants and/or to control phytopathogenic fungi and/or to control unwanted plant growth, with seeds of crop plants being treated with the composition.

The present invention also provides plant propagation material comprising the amphiphile. The agrochemical formulations can also be used to control unwanted insect or mite infestation on plants and/or to control phytopathogenic fungi and/or to control unwanted plant growth, with plant propagation materials of crop plants being treated with the amphiphile of the invention.

Plant propagation materials can be treated preventively in conjunction with or even before sowing, and/or in conjunction with or even before planting out, with the amphiphile as such or with a composition comprising at least one amphiphile. For treating plant propagation materials, more particularly seed, it is usual to use water-soluble concentrates (LS), suspensions (FS), dusts (DS), water-dispersible and water-soluble powders (WS, SS), emulsions (ES), emulsifiable concentrates (EC), and gels (GF). These compositions may be applied neat or, preferably, diluted to the propagation materials, more particularly seed. The composition in question may be diluted 2 to 10 times, giving 0.01% to 60% by weight, preferably 0.1% to 40% by weight, of active compound in the compositions used for seed dressing. Application may take place before or during sowing.

The treatment of plant propagation material, more particularly the treatment of seed, is known to the skilled worker and takes place by dusting, coating, pelletizing, dipping or drenching the plant propagation material, the treatment taking place preferably by pelletizing, coating, and dusting, or by furrow treatment, in order, for example, to prevent premature germination of the seed. Treatment with the amphiphile may optionally comprise treatment with a pesticide, in which case the treatment with the pesticide may take place at the same time, before or after the treatment with the amphiphile.

For seed treatment it is preferred to use suspensions. Such compositions typically comprise 1 to 800 g/l of active compound, 1 to 200 g/l of surfactants, 0 to 200 g/l of antifreeze agents, 0 to 400 g/l of binders, 0 to 200 g/l of dyes and solvents, preferably water. In the treatment of plant propagation materials, such as seed, it is general practice to use active compound quantities of 0.1 to 1000 g/100 kg of propagation material or seed, preferably 1 to 1000 g/100 kg, more preferably 1 to 100 g/100 kg, more particularly 5 to 100 g/100 kg.

Application of amphiphile separately from or together simultaneously with at least one pesticide is possible. Application together in the sense of the present specification means that the at least one amphiphile and the at least one pesticide are present in sufficient quantity, simultaneously, at the site of action (e.g., the phytopathogenic fungi to be controlled, and their habitat, such as infested plants, plant propagation materials, more particularly seed, soil, materials or spaces, and also plants, plant propagation materials, more particularly seed, soils, materials or spaces that are to be protected from fungal infestation). This can be accomplished by delivering the amphiphile and at least one pesticide together, simultaneously, in a joint active compound preparation or in at least two separate active compound preparations, or by applying the substances in succession at the site of action, the time spacing between the individual applications being selected such that the compound applied first is present in sufficient amount at the site of action at the time when the further active compound or compounds is/are applied. The time sequence of the delivery of the compounds is of minor importance.

The invention also provides an amphiphile comprising a hyperbranched polycarbonate which is joined to at least one linear or comb-type polymer, wherein the linear polymer is
a) a homopolymer or random copolymer comprising a polar ethylenically unsaturated monomer,
b) a block polymer comprising a block of polyethylene glycol or based on a polar ethylenically unsaturated monomer,
c) a polycondensate comprising polyethylene glycol, or
d) a polyethylene glycol,
the polyethylene glycol d) being joined to the polycarbonate via a linker.

Suitable and preferably linear or comb-type polymers are as described above. With particular preference the linear polymer is one of the aforementioned polymers a), b) or c). In another particularly preferred embodiment the linear polymer is one of the aforementioned polymers a), c) or d). With very particular preference the linear polymer is one of the aforementioned polymers a) or c). With especial preference the comb-type polymer comprises polyethylene glycol mono(meth)acrylate in polymerized form. A preferred linker is a polyisocyanate.

The hyperbranched polycarbonate is typically obtainable by
a) preparing a condensation product (K) by reacting an organic carbonate (A) or a phosgene derivative with an alcohol (B1) which has at least three hydroxyl groups, and
b) intermolecularly converting K to the hyperbranched polycarbonate,
the quantitative ratio of the OH groups to the carbonate or phosgene groups being selected such that K has an average of either i) one carbonate or carbamoyl chloride group and more than one OH group, or ii) one OH group and more than one carbonate or carbamoyl group. Other preferred embodiments of the hyperbranched polycarbonate have been described above.

The invention also provides a process for preparing the amphiphile of the invention, by reacting the polycarbonate, the linear or comb-type polymer, and a linker. Preferred linkers and reaction conditions are as described above. The amphiphile preferably is obtainable by
a) providing the hyperbranched polycarbonate and the linear or comb-type polymer, and then
b) joining the components with the linker.

With particular preference the amphiphile is obtained in this way. The linker is preferably a diisocyanate.

The invention additionally provides for the use of an amphiphile in compositions comprising an active ingredient whose solubility in water at 20° C. is not more than 10 g/L, the amphiphile comprising a hyperbranched polycarbonate. The hyperbranched polycarbonate is preferably joined to a linear or comb-type polymer and/or to a functional $C_1$-$C_{24}$ unit comprising an acid group, an amino group or at least two hydroxyl groups. In another embodiment the invention provides for the use of an amphiphile in compositions comprising an active ingredient whose solubility in water at 20° C. is not more than 10 g/L, the amphiphile comprising a hyperbranched polycarbonate which is joined to at least one linear or comb-type polymer, the linear polymer being
a) a homopolymer or random copolymer comprising a polar ethylenically unsaturated monomer,
b) a block polymer comprising a block of polyethylene glycol or based on a polar ethylenically unsaturated monomer,
c) a polycondensate comprising polyethylene glycol, or
d) a polyethylene glycol,
the polyethylene glycol d) being joined to the polycarbonate via a linker.

Preferred active ingredients are active agrochemical ingredients, active cosmetic ingredients, active pharmaceutical ingredients or nutritional supplements (such as vitamins and carotenoids), more particularly active agrochemical ingredients.

Advantages of the present invention are that a high concentration of active compound can be brought into solution, that the preparation of the amphiphile from pre-prepared polymers can be accomplished very easily and industrially by means of a linker, that the linear or comb-type polymers (more particularly the random copolymers and the polar homopolymers and also polyethylene glycol) are very easy to obtain and can even be optimized for particular amphiphiles, that the amphiphile itself is water-soluble or water-dispersible, or that it is less sensitive to hydrolysis than are many polyesters. A further advantage is that, as a result of the preferred use of a polyisocyanate as linker, the reaction of isocyanate groups produces additional urethane bonds or urea bonds, thereby increasing the hydrophobic fraction of the amphiphile. As a result, in comparison to other modified, hyperbranched polycarbonates, the amphiphiles of the invention exhibit significantly further-improved solubilization properties.

The examples which follow illustrate the invention without restricting it.

EXAMPLES

TMP×5.2 PO: Reaction product of trimethylolpropane with a 5.2 molar excess of propylene oxide (PO).
TMP×15.7 PO: Reaction product of trimethylolpropane with 15.7 molar excess of propylene oxide.
Gly×5.7 PO: Reaction product of glycerol with a 5.7 molar excess of PO.
PE×5.0 EO: Reaction product of pentaerythritol with a 5.0 molar excess of ethylene oxide
DBTL: Dibutyltin dilaurate
IPDI: Isophorone diisocyanate
AIBN: Azobis(isobutyronitrile)
PEGMEMA 475: Polyethylene glycol monomethyl ether methacrylate (M=475 g/mol)

The hyperbranched polymers were analyzed by gel permeation chromatography using a refractometer as detector. The mobile phase used was dimethylacetamide, while the standard used for determining the molecular weight was polymethyl methacrylate (PMMA). The OH number was determined in accordance with DIN 53240, part 2. The molar masses of the linearly dendritic copolymers were determined arithmetically from the number-average molecular weight of the parent hyperbranched core, its OH number, and the degree of functionalization selected (stoichiometric ratio of NCO groups of functional linear polymers/available OH groups of core molecule) (assumption of a quantitative addition reaction of the linker-reactive groups to the linker).

Synthesis Example 1

Hyperbranched Polycarbonate Having Terminal Carboxylic Acid Groups (A.1)

3010 g of the trifunctional alcohol TMP×5.2 PO, 1075 g of diethyl carbonate and 0.5 g of catalyst KOH were introduced. The reaction mixture was heated to boiling and stirred until, as a result of the evaporative cooling of the ethanol liberated, the boiling temperature of the reaction mixture had dropped to a constant temperature (around 126° C.). Then ethanol was distilled off and the temperature of the reaction mixture was increased slowly to 190° C. Ethanol was collected in a cooled round-bottomed flask and weighed, and in this way the conversion rate was determined by comparison with the theoretically possible complete conversion, as a percentage. When a conversion rate of 85% was reached, the reaction was brought to a pH of 7 by addition of 85% strength phosphoric acid. Subsequently, at 130° C. under a pressure of 100 mbar, residual volatiles were removed over 30 minutes, and the batch was then cooled to room temperature.

258 g of the resultant product were admixed with 78 g of succinic anhydride and the mixture was heated to 130° C. After 140 minutes it was cooled, and the succinic anhydride which had sublimed in the reflux condenser was returned to the reaction by addition of 46 g of acetone. With distillative removal of the acetone, the reaction mixture was heated to 130° C. again over 1 hour and was held at that temperature for a further 30 minutes. It was then cooled to room temperature.

The polymer A.1 ($M_n$=3100 g/mol; $M_w$=61 700 g/mol; OH number: 37 mg KOH/g polymer; acid number: 135 mg KOH/g polymer) was obtained in the form of a yellow-colored, high-viscosity liquid, which following neutralization of 75% of the terminal carboxylic acid groups with triethanolamine had a very good water solubility. The polymer A.1 was used in this partially neutralized form for the further experiments.

Synthesis Example 2

Hyperbranched Polycarbonate Core Having Terminal Hydroxyl Groups (A.2)

2298 g of TMP×15.7 PO, 284 g of diethyl carbonate and 2 g of catalyst DBTL were introduced and heated to boiling. The boiling reaction mixture was stirred until (about 14 hours) the boiling temperature of the reaction mixture, as a result of the evaporative cooling of the liberated ethanol, had dropped to a constant temperature of around 143° C. The reflux condenser was then replaced by a distillation bridge, and the ethanol formed in the reaction was distilled off, the temperature of the reaction mixture being increased to up to 230° C. The ethanol was collected in a cooled round-bottomed flask and weighed, and in this way the conversion rate was determined in relation to the theoretically possible complete conversion, as a percentage. When a conversion rate of 89% had been reached, dry nitrogen was passed through the reaction mixture at a temperature of 160° C. for 1 hour in order to remove any remaining quantities of monomers. Thereafter the batch was cooled to room temperature.

The polymer A.2 ($M_n$=2400 g/mol; $M_w$=4600 g/mol; OH number: 87 mg KOH/g polymer) was obtained in the form of a yellow-colored, high-viscosity liquid which was not water soluble.

Synthesis Example 3

Hyperbranched Polycarbonate Core Having Terminal Hydroxyl Groups (A.3)

1149 g of the trifunctional alcohol of TMP×15.7 PO, 144 g of diethyl carbonate and 1 g of catalyst DBTL were reacted as in synthesis example 2. The polymer A.3 ($M_n$=4200 g/mol; $M_w$=14 500 g/mol; OH number: 85 mg KOH/g polymer) was obtained in the form of a yellow-colored, high-viscosity liquid which was not water soluble.

Synthesis Example 4

Hyperbranched Polycarbonate Core Having Terminal Hydroxyl Groups (A.4)

2000 g of the trifunctional alcohol Gly×5.7 PO, 562 g of diethyl carbonate and 0.4 g of catalyst KOH were introduced and heated at boiling until the boiling temperature of the reaction mixture, as a result of the evaporative cooling of the liberated ethanol, had dropped to a constant temperature of around 113° C. The reflux condenser was then replaced by a distillation bridge, and the ethanol formed in the reaction was distilled off, the temperature of the reaction mixture being increased to 200° C. Ethanol was collected in a cooled round-bottomed flask and weighed, and in this way the conversion rate was determined in relation to the theoretically possible complete conversion, as a percentage. When a conversion rate of 80% had been reached, the reaction mixture was cooled to 100° C. and adjusted to a pH of 7 by addition of 0.45 g of 85% strength phosphoric acid. Subsequently the reaction mixture was heated to 200° C. again and, at this temperature, dry nitrogen was passed through the mixture for a period of 3.5 hours in order to remove any remaining amounts of monomers. Thereafter the batch was cooled to room temperature.

The polymer A.4 ($M_n$=1700 g/mol; $M_w$=3300 g/mol; OH number: 206 mg KOH/g polymer) was obtained in the form of a yellow-colored, high-viscosity liquid which was not water soluble.

Synthesis Example 5

Hyperbranched Polycarbonate Core A.2 Functionalized with PEG Chains (Degree of Functionalization 100%, A.5)

Stage 1 (A.5a): 123.5 g of polyethylene glycol monomethyl ether ($M_n$=500 g/mol) were introduced and freed from residues of water under reduced pressure at 80° C. After it had cooled to room temperature, the batch was placed under nitrogen and the polymer was dissolved in 123.5 g of butyl acetate. Then 50.0 g of isophorone diisocyanate were added and the mixture was heated to 50° C. By addition of 19 mg of zinc neodecanoate in solution in 1 ml of butyl acetate, the reaction was initiated and was run over the course of 3.5 hours at 50° C. to an NCO content of 2.87%. The reaction was then ended by cooling to −20° C. The reaction product A.5a was used directly, without further work-up, in stage 2.

Stage 2 (A.5): 30.1 g of the hydrophobic hyperbranched polycarbonate core A.2 were introduced and were admixed under nitrogen with 71.0 g of the reaction mixture A.5a. The batch was then heated to 80° C. and the reaction was initiated by addition of 7 mg of DBTL in solution in 1 ml of butyl acetate. Following complete conversion of all the NCO groups (NCO content 0%), the batch was cooled and the solvent was removed under reduced pressure. Finally the linearly dendritic copolymer A.5 ($M_n$=5070 g/mol) was obtained, in the form of a yellow-colored, high-viscosity liquid which was fully water soluble.

Synthesis Example 6

Hyperbranched Polycarbonate Core A.3 Functionalized with Peg Chains (Degree of Functionalization 100%, A.6)

Stage 1 (A.6a): 247.5 g of polyethylene glycol monomethyl ether ($M_n$=500 g/mol) were introduced and freed from residues of water under reduced pressure at 80° C. After it had cooled to room temperature, the batch was placed under nitrogen and the polymer was dissolved in 247.5 g of butyl acetate. Then 100.0 g of IPDI were added and the mixture was heated to 50° C. By addition of 37 mg of zinc neodecanoate in solution in 1 ml of butyl acetate, the reaction was initiated and was run over the course of about 3 hours at 50° C. to an NCO content of 2.88%. The reaction was then ended by cooling to −20° C. The reaction product A.6a was used directly, without further work-up, in stage 2. Stage 2 (A.6): 25.0 g of the hydrophobic hyperbranched polycarbonate core A.3 were introduced and were dissolved under nitrogen in 25.0 g of butyl acetate. The batch was admixed with 60.25 g of the reaction mixture A.6a, and heated to 80° C., and the reaction was initiated by addition of 80 mg of DBTL in solution in 1 ml of butyl acetate. Following complete conversion of all the NCO groups (NCO content 0%), the batch was cooled and the solvent was removed under reduced pressure. Finally the linearly dendritic copolymer A.6 ($M_n$=8810 g/mol) was obtained, in the form of a yellow-colored, high-viscosity liquid which was fully water soluble.

Synthesis Example 7

Hyperbranched Polycarbonate Core A.3 Functionalized with a Comb-Type PMMA-Co-PS-co-PEGMEMA Copolymer (Degree of Functionalization 100%, A.7)

Stage 1 (A.7a): 250.0 g of tetrahydrofuran (THF) were introduced under nitrogen and then heated under reflux. Over the course of 2 hours, a mixture 1 of 180.2 g of methyl methacrylate (MMA), 70.3 g of styrene and 214.0 g of PEGMEMA 475 and also, simultaneously over the course of 4 hours, a mixture 2 of 8.6 g of AIBN and 27.0 g of mercaptoethanol in solution in 250.0 g of THF were run slowly into the batch using two metering pumps. After the end of addition of mixture 2, the reaction mixture was heated under reflux for a further 16 hours. Subsequent monitoring of the residual monomers by GC gave an MMA fraction of <1%, and so the batch was cooled and the product A.7a ($M_n$=1030 g/mol) was used further directly in stage 2.

Stage 2 (A.7b): 300.0 g of reaction mixture A.7a were introduced and freed from the THF solvent under reduced pressure. After it had cooled to room temperature, the batch was placed under nitrogen and the residue was dissolved in 152.0 g of butyl acetate. Then 20.94 g of isophorone diisocyanate were added and the mixture was heated to 50°

C. By addition of 30 mg of zinc neodecanoate in solution in 1 mL of butyl acetate, the reaction was started and was run to an NCO content of 1.09% at 50° C. over the course of approximately 7 hours. Thereafter the reaction was ended by cooling to −20° C. The reaction product A.7b was used without further work-up directly in stage 3.

Stage 3 (A.7): 20.0 g of the hydrophobic hyperbranched polycarbonate core A.3 were introduced and dissolved under nitrogen in 20.0 g of butyl acetate. The batch was then admixed with 127.0 g of the reaction mixture A.7b and heated to 80° C., and the reaction was initiated by addition of 84 mg of DBTL in solution in 1 mL of butyl acetate. Following the complete conversion of all the NCO groups (NCO content 0%), the batch was cooled and the solvent was removed under reduced pressure. Finally the linearly dendritic copolymer A.7 ($M_n$=12200 g/mol) was obtained in the form of a yellow-colored, high-viscosity liquid, which was fully water soluble.

Synthesis Example 8

Hyperbranched Polycarbonate Core Functionalized with a Comb-Type PVP-co-Plauryl acrylate-co-PEGMEMA (Degree of Functionalization 30%, A.8)

Stage 1 (A.8a): 100.0 g of THF were introduced under nitrogen and then heated under reflux. Over the course of 3 hours, a mixture 1 of 155.9 g of lauryl acrylate, 144.2 g of N-vinylpyrrolidone and 163.3 g of PEGMEMA 475 in solution in 200.0 g of THF, and also, simultaneously over the course of 4 hours, a mixture 2 of 8.8 g of AIBN and 27.8 g of mercaptoethanol in solution in 200.0 g of THF were run slowly into the batch using two metering pumps. After the end of addition of mixture 2, the reaction mixture was heated under reflux for a further 18 hours. Subsequent monitoring of the residual monomers by GC gave a lauryl acrylate fraction of <1%, and so the batch was cooled and the product A.8a ($M_n$=1000 g/mol) was used further directly in stage 2.

Stage 2 (A.8b): 278.4 g of reaction mixture A.8a were introduced and freed from the THF solvent under reduced pressure. After it had cooled to room temperature, the batch was placed under nitrogen and the residue was dissolved in 140.0 g of butyl acetate. Then 20.0 g of isophorone diisocyanate were added and the mixture was heated to 50° C. By addition of 21 mg of zinc neodecanoate in solution in 1 mL of butyl acetate, the reaction was started and was run to an NCO content of 1.16% at 60° C. for 6 hours and also at room temperature for a total of 16 hours. Thereafter the reaction was ended by cooling to −20° C. The reaction product A.8b was used without further work-up directly in stage 3.

Stage 3 (A.8): 6.0 g of the hydrophobic hyperbranched polycarbonate core A.3 were introduced and dissolved under nitrogen in 6.0 g of butyl acetate. The batch was then admixed with 11.4 g of the reaction mixture A.8b and heated to 80° C., and the reaction was initiated by addition of 12 mg of DBTL in solution in 1 mL of butyl acetate. Following the complete conversion of all the NCO groups (NCO content 0%), the batch was cooled and the solvent was removed under reduced pressure. Finally the linear dendritic copolymer A.8 ($M_n$=6540 g/mol) was obtained in the form of a yellow-colored, high-viscosity liquid, which was fully water soluble.

Synthesis Example 9

Hyperbranched Polycarbonate Core Functionalized with a Comb-Type PVP-co-Plauryl acrylate-co-PEGMEMA Copolymer (Degree of Functionalization 50%, A.9)

Stage 1 (A.9a): 100.0 g of THF were introduced under nitrogen and then heated under reflux. Over the course of 3 hours, a mixture 1 of 155.9 g of lauryl acrylate, 144.2 g of N-vinylpyrrolidone and 163.3 g of PEGMEMA 475 in solution in 200.0 g of THF, and also, simultaneously over the course of 4 hours, a mixture 2 of 8.8 g of AIBN and 27.8 g of mercaptoethanol in solution in 200.0 g of THF were run slowly into the batch using two metering pumps. After the end of addition of mixture 2, the reaction mixture was heated under reflux for a further 18 hours. Subsequent monitoring of the residual monomers by GC gave a lauryl acrylate fraction of <1%, and so the batch was cooled and the product A.9a ($M_n$=1000 g/mol) was used further directly in stage 2.

Stage 2 (A.9b): 278.4 g of reaction mixture A.9a were introduced and freed from the THF solvent under reduced pressure. After it had cooled to room temperature, the batch was placed under nitrogen and the residue was dissolved in 140.0 g of butyl acetate. Then 20.0 g of isophorone diisocyanate were added and the mixture was heated to 50° C. By addition of 21 mg of zinc neodecanoate in solution in 1 mL of butyl acetate, the reaction was started and was run to an NCO content of 1.16% at 60° C. for 6 hours and also at room temperature for a total of 16 hours. Thereafter the reaction was ended by cooling to −20° C. The reaction product A.9b was used without further work-up directly in stage 3.

Stage 3 (A.9): 6.0 g of the hydrophobic hyperbranched polycarbonate core A.3 were introduced and dissolved under nitrogen in 6.0 g of butyl acetate. The batch was then admixed with 19.2 g of the reaction mixture A.9b and heated to 80° C., and the reaction was initiated by addition of 13 mg of DBTL in solution in 1 mL of butyl acetate.

Following the complete conversion of all the NCO groups (NCO content 0%), the batch was cooled and the solvent was removed under reduced pressure. Finally the linearly dendritic copolymer A.9 ($M_n$=8110 g/mol) was obtained in the form of a yellow-colored, high-viscosity liquid, which was fully water soluble.

Synthesis Example 10

Hyperbranched Polycarbonate Core A.3 Functionalized with PEG-b-Polycaprolactone Block Copolymer (Degree of Functionalization 100%, A.10)

Stage 1 (A.10a): 150.0 g of polyethylene glycol monomethyl ether ($M_n$=500 g/mol) were introduced and were freed from residues of water under reduced pressure at 90° C. After it had cooled to room temperature, the batch was placed under nitrogen and the polymer was admixed with 205.0 g of ε-caprolactone. The mixture was heated to 90° C. and the ring-opening polymerization of the caprolactone was initiated by addition of 355 mg of butyltin tris(2-ethylhexanoate). The batch was heated at 90° C. for a further 18 hours and after the end of reaction was cooled to room temperature. The resultant OH-terminated block copolymer A.10a ($M_n$=1180 g/mol) was used directly without further purification in stage 2.

Stage 2 (A.10b): 200.0 g of the block copolymer A.10a were introduced and placed under nitrogen, and 34.1 g of isophorone diisocyanate were added. The mixture was heated to 50° C. By addition of 30 mg of zinc neodecanoate in solution in 1 mL of butyl acetate, the reaction was initiated and was run to an NCO content of 2.23% at 50° C. over the course of 4 hours. Thereafter the reaction mixture was ended by cooling to −20° C. The reaction product A.10b was used directly, without further work-up, in stage 3.

Stage 3 (A.10): 7.0 g of the hydrophobic hyperbranched polycarbonate core A.3 were introduced and were dissolved under nitrogen in 10.0 g of butyl acetate. The batch was then admixed with 20.0 g of the reaction mixture A.10b and heated to 80° C., and the reaction was initiated by addition of 27 mg of DBTL in solution in 1 mL of butyl acetate. Following the complete conversion of all the NCO groups (NCO content 0%), the batch was cooled and the solvent was removed under reduced pressure. Finally the linearly dendritic copolymer A.10 ($M_n$=13 190 g/mol) was obtained in the form of a yellow-colored, high-viscosity liquid which was fully water soluble.

Synthesis Example 11

Hyperbranched Polycarbonate Core A.4 Functionalized with PEG-b-PU Block Copolymer (Degree of Functionalization 100%, A.11)

Stage 1 (A.11a): 23.4 g of neopentyl glycol and 20.3 g of 1,3-butanediol were dissolved in 100.0 g of THF. The batch was placed under nitrogen and admixed with 100.8 g of hexamethylene diisocyante (HDI) in solution in 44.5 g of THF. The exothermic reaction was initiated by addition of 140 mg of zinc neodecanoate in solution in 1 mL of THF, and was apparent from an increase in temperature to around 50° C. Thereafter, an internal temperature of 50° C. was maintained and the batch was run to an NCO content of 4.40% at 50° C. over the course of 7.5 hours. Then a solution of 300.0 g of polyethylene glycol monomethyl ether ($M_n$=2000 g/mol) in 300.0 g of THF was added to the reaction mixture, which was heated at 50° C. for 4 hours more. When an NCO content of 0.79% had been reached, the reaction was ended by cooling to −20° C. The reaction product A.11a ($M_n$=2960 g/mol) was used directly, without further work-up, in stage 2.

Stage 2 (A.11): 3.0 g of the hydrophobic hyperbranched polycarbonate core A.4 were introduced and were admixed under nitrogen with 75.5 g of the reaction product A.11a, giving a clear solution. The batch was then heated to 50° C. and the reaction was initiated by addition of 2 mg of DBTL in solution in 1 mL of butyl acetate. Following the complete conversion of all of the NCO groups (NCO content 0%), the batch was cooled and the solvent THF was removed under reduced pressure. Finally the linearly dendritic copolymer A.11 ($M_n$=20 350 g/mol) was obtained in the form of a yellow-colored, high-viscosity liquid which was fully water soluble.

Synthesis Example 12

Preparation of a Polycarbonate Having a Polar Core and Terminal OH Groups (A.12)

2000 g of the tetrafunctional alcohol PE×5.0 EO, 665 g of diethyl carbonate and 0.4 g of catalyst KOH were introduced and heated at boiling (about 5 hours) until the boiling temperature of the reaction mixture, as a result of the evaporative cooling of the liberated ethanol, had dropped to a constant temperature of around 105° C. The reflux condenser was then replaced by a distillation bridge, and the ethanol formed in the reaction was distilled off, the temperature of the reaction mixture being increased to 190° C. Ethanol was collected in a cooled round-bottomed flask and weighed, and in this way the conversion rate was determined in relation to the theoretically possible complete conversion, as a percentage. When a conversion rate of 90% had been reached, the reaction mixture was cooled to 100° C. and adjusted to a pH of <7 by addition of 0.4 g of 85% strength phosphoric acid. Subsequently the reaction mixture was heated to 200° C. again and, at this temperature, dry nitrogen was passed through the mixture for a period of 5 hours in order to remove any remaining amounts of monomers. Thereafter the batch was cooled to room temperature. The polymer A.12 ($M_n$=3200 g/mol; $M_w$=22 100 g/mol; OH number: 335 mg KOH/g polymer) was obtained in the form of a yellow-colored, high-viscosity liquid which was water soluble.

Synthesis Example 13

Hyperbranched Polycarbonate Core Functionalized with PEG Chains (A.13)

2000 g of TMP×15.7 PO, 247 g of diethyl carbonate and 1.7 g of DBTL catalyst were reacted as in synthesis example 2 to give a hyperbranched polycarbonate core (Mn=3000 g/mol, Mw=6200 g/mol, OH number=87 mg KOH/g). The resultant polycarbonate core was ethoxylated with ethylene oxide by reaction in a weight ratio of core to ethylene oxide of 1 to 1. This was done by placing the core in a pressurized autoclave and adding a 50% strength aqueous KOH solution. After the reaction mixture had been rendered inert using nitrogen, the batch was freed from residual water at 120° C. under reduced pressure. Then ethylene oxide was added to the reaction mixture. After the end of ethylene oxide metering and the attainment of a constant reactor pressure, unreacted ethylene oxide and other volatiles were removed by distillation under reduced pressure, and the ethoxylated polymer was taken from the polymerization reactor and worked up in a standard manner. This gave the linear-dendritic copolymer A.13 (OH number 47 mg KOH/g polymer) in the form of a yellow-colored, highly viscous liquid which was fully soluble in water.

Solubilization Experiments:

The wavelengths of the UV-spectroscopic measurements (if applicable) are summarized in table 1.

TABLE 1

| Compound to be dissolved | Wavelength of UV measurement [nm] |
|---|---|
| Piroxicam | 356 |
| Carbamazepine | 286 |
| Estradiol | 282 |
| Clotrimazole | HPLC analysis |
| Pyrene | 334 |
| Pyraclostrobin | 277 |
| Fipronil | 280 |

General Procedure 1 for Solubilization Experiments with Piroxicam, Carbamazepine, Estradiol and Clotrimazole Approximately 2 g of polymer were weighed out into a 50 mL glass beaker. Then 0.2 g of each active ingredient was weighed into the batch to give a supersaturated solution. Next, phosphate buffer pH 7.0 was added in an amount such as to give a polymer:phosphate buffer mass ratio of 1:9. The mixture was then stirred at room temperature for 72 hours, using a magnetic stirrer. After a rest time of one hour, unsolubilized active ingredient was removed by filtration. The resulting clear or opaque solution was then analyzed for its active ingredient content by means of UV spectroscopy or HPLC.

TABLE 2

| Solubility [mg/l] in the presence of | Piroxicam | Carbamazepine | Estradiol | Clotrimazole |
|---|---|---|---|---|
| Without polymer[a] | 420 | 140 | <100 | <100 |
| Polymer A.1 | 1600 | 1500 | 400 | 3600 |
| Polymer A.5 | 4400 | 1600 | 700 | 700 |
| Polymer A.6 | 3100 | 1250 | 1080 | 2430 |
| Polymer A.7 | 2410 | 1390 | 1190 | 1830 |
| Polymer A.8 | 2430 | 1440 | 1950 | 2160 |
| Polymer A.9 | 2670 | 1230 | 2360 | 1620 |

[a] not inventive

General Procedure 2 for Solubilization Experiments with Pyrene, Pyraclostrobin and Fipronil Approximately 100 mg of polymer were weighed out into a 50 mL glass beaker and dissolved in 9.900 g of distilled water. Then 100 mg of each active ingredient was weighed into the batch to give a supersaturated solution. The mixture was then stirred at room temperature for 24 hours, using a magnetic stirrer. After a rest time of one hour, unsolubilized active ingredient was removed by centrifuging. The resulting clear or opaque solution was then analyzed for its active ingredient content by means of UV spectroscopy.

TABLE 3

| Solubility [mg/l] in the presence of | Pyrene | Pyraclostrobin | Fipronil |
|---|---|---|---|
| Without polymer[a] | 0.1 | 22.5 | 3 |
| Polymer A.1 | 132 | 626 | 79 |
| Polymer A.5 | 143 | 765 | 312 |
| Polymer A.6 | 172 | n.d. | 240 |
| Polymer A.7 | 263 | 1148 | 462 |
| Polymer A.8 | 317 | n.d. | 828 |
| Polymer A.9 | 283 | n.d. | 667 |
| Polymer A.10 | 280 | n.d. | 654 |
| Polymer A.11 | 25 | 225 | n.d. |
| Polymer A.12[a] | <1 | <30 | n.d. | n.d.: not determined;
[a] not inventive

Comparison of the Solubilizing Properties of Core, Shell, Core/Shell Blends and Inventive Linearly Dendritic Block Copolymer The solubility was determined as described in procedure 2.

TABLE 4a

| Solubility [mg/l] in the presence of | Pyrene | Fipronil | Water solubility of the polymer |
|---|---|---|---|
| Without polymer [a] | 0.1 | 3 | — |
| Polymer A.5 | 143 | 312 | Yes |
| Polymer A.2 (core only) [a] | — | — | No |
| PEG monomethyl ether (shell only) [a] | 3 | 6 | Yes |
| Polymer A.2 + PEG monomethyl ether (mixture of core + shell) [a] | — | — | No (undissolved fractions) |

[a] not inventive

Table 4a shows that the inventive functionalized polycarbonate A.5 (A.2 functionalized with PEG monomethyl ether) has higher solubilizing capacities than the individual constituents, i.e., the core polymer (A.2), the shell polymer (PEG monomethyl ether) or the mixture (i.e., no covalent joining) of core polymer and shell polymer.

TABLE 4b

| Solubility [mg/l] in the presence of | Pyrene | Fipronil | Water solubility of the polymer |
|---|---|---|---|
| Without polymer [a] | 0.1 | 3 | — |
| Polymer A.8 | 317 | 828 | Yes |
| Polymer A.3 (core only) [a] | — | — | No |
| Polymer A.8a (shell only) [a] | 171 | 366 | Yes |
| Polymer A.3 + Polymer A.8a (mixture of core + shell) [a] | — | — | No (undissolved mixtures) |

[a] not inventive

Table 4b shows that the inventive functionalized polycarbonate A.8 (A.3 functionalized with A.8a) has higher solubilizing capacities than the individual constituents, i.e., the core polymer (A.3), the shell polymer (polymer A.8a) or the mixture (i.e., no covalent joining) of core polymer and shell polymer.

The invention claimed is:

1. A composition comprising an amphiphile and an active agrochemical ingredient whose solubility in water at 20° C. is not more than 10 g/L, wherein the amphiphile comprises a hyperbranched polycarbonate which is joined to at least one linear or comb-type polymer, the linear polymer being
   b) a block polymer comprising a block of polyethylene glycol, or
   c) a polycondensate or polyaddition product comprising polyethylene glycol, or
   d) a polyethylene glycol,
   the polyethylene glycol d) being joined to the polycarbonate via a linker, and
   wherein the linker is selected from toluene 2,4-diisocyanate, toluene 2,6-diisocyanate, 2,4-diphenylmethane diisocyanate, cis- and trans-isophorone diisocyanate, or mixtures of these compounds; and
   wherein the polycarbonate comprises an alcohol (B1) which is a polyetherol based on alcohols selected from glycerol, trimethylolethane, trimethylolpropane, 1,2,4-butanetriol, 1,2,3-hexanetriol, 1,2,4-hexanetriol, pentaerythritol, or mixtures thereof, and the polyetherol comprises 3 to 20 propylene oxide units in polymerized form.

2. The composition according to claim 1, wherein the polyethylene glycol is a polyethylene glycol or polyethylene glycol monoalkyl ether having a molar mass Mn of at least 200 g/mol.

3. The composition according to claim 1, wherein the comb-type polymer comprises polyethylene glycol mono(meth)acrylate or allyl alcohol alkoxylate in polymerized form.

4. The composition according to claim 1, wherein the amphiphile comprises a hyperbranched polycarbonate which is joined to at least one linear or comb-type polymer.

5. An amphiphile comprising a hyperbranched polycarbonate which is joined to at least one linear or comb-type polymer, wherein the linear polymer is
   b) a block polymer comprising a block of polyethylene glycol,
   c) a polycondensate or polyaddition product comprising polyethylene glycol, or d) a polyethylene glycol, the polyethylene glycol d) being joined to the polycarbonate via a linker, wherein the linker is selected from toluene 2,4-diisocyanate, toluene 2,6-diisocyanate, 2,4-diphenylmethane diisocyanate, cis- and trans-isophorone diisocyanate, or mixtures of these compounds; and wherein the polycarbonate comprises an alcohol (B1) which is a polyetherol based on alcohols selected from glycerol, trimethylolethane, trimethylolpropane, 1,2,4-butanetriol, 1,2,3-hexanetriol, 1,2,4-hexanetriol, pentaerythritol, or mixtures thereof, and the polyetherol comprises 3 to 20 propylene oxide units in polymerized form.

6. The amphiphile according to claim 5, wherein the polycarbonate is obtainable by
 a) preparing a condensation product (K) by reacting an organic carbonate (A) or a phosgene derivative with an alcohol (B1) which has at least three hydroxyl groups, and
 b) intermolecularly converting the condensation product K to the hyperbranched polycarbonate,
 the quantitative ratio of the OH groups to the carbonate or phosgene groups being selected such that the condensation product K has an average of either i) one carbonate or carbamoyl chloride group and more than one OH group, or ii) one OH group and more than one carbonate or carbamoyl group.

7. The amphiphile according to claim 5, wherein the comb-type polymer comprises polyethylene glycol mono(meth)acrylate in polymerized form.

8. The amphiphile according to claim 5, wherein the polyethylene glycol is a polyethylene glycol or polyethylene glycol monoalkyl ether having a molar mass Mn of at least 200 g/mol.

9. A process for preparing the amphiphile according to claim 5, comprising reacting the polycarbonate with the linear or comb-type polymer and a linker.

10. A method for controlling phytopathogenic fungi, or unwanted plant growth, or unwanted insect or mite infestation, or for regulating the growth of plants, comprising contacting the composition of claim 5 on the respective pests, their habitat or the plants to be protected from the respective pest, or on the soil and/or on unwanted plants and/or the crop plants and/or their habitat.

11. The method of claim 10, wherein the polyethylene glycol is a polyethylene glycol or polyethylene glycol monoalkyl ether having a molar mass Mn of at least 200 g/mol.

12. The method of claim 10, wherein the comb-type polymer comprises polyethylene glycol mono(meth)acrylate or allyl alcohol alkoxylate in polymerized form.

13. A plant propagation material treated with the amphiphile according to claim 5.

14. The composition according to claim 1, wherein the alcohol (B1) is a trifunctional polyetherol based on glycerol, trimethylolethane, trimethylolpropane, 1,2,4-butanetriol and/or pentaerythritol, and propylene oxide, where the polyetherol comprises three to 20 propylene oxide units in polymerized form.

15. The amphiphile according to claim 5, wherein the alcohol (B1) is a trifunctional polyetherol based on glycerol, trimethylolethane, trimethylolpropane, 1,2,4-butanetriol and/or pentaerythritol, and propylene oxide, where the polyetherol comprises three to 20 propylene oxide units in polymerized form.

16. The composition according to claim 1, wherein the active agrochemical ingredient is fipronil.

\* \* \* \* \*